(12) United States Patent
Khosla et al.

(10) Patent No.: US 11,160,562 B2
(45) Date of Patent: Nov. 2, 2021

(54) ASSEMBLIES FOR PREPARATION OF SURGICAL SITES

(71) Applicant: Arthrex, Inc., Naples, FL (US)

(72) Inventors: Rudraksh Khosla, Naples, FL (US); Michael Alan Knight, Naples, FL (US); Mark Wise, Bonita Springs, FL (US); Dean Hutchinson, Naples, FL (US); John David Paterson, Naples, FL (US); Tyler Clevett, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 31 days.

(21) Appl. No.: 16/738,005

(22) Filed: Jan. 9, 2020

(65) Prior Publication Data

US 2021/0212701 A1 Jul. 15, 2021

(51) Int. Cl.
| | | |
|---|---|---|
| *A61B 17/16* | (2006.01) | |
| *A61B 17/17* | (2006.01) | |
| *A61B 90/00* | (2016.01) | |

(52) U.S. Cl.
CPC ...... *A61B 17/1615* (2013.01); *A61B 17/1631* (2013.01); *A61B 17/17* (2013.01); *A61B 2090/062* (2016.02)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1631; A61B 17/1633
See application file for complete search history.

(56) References Cited

U.S. PATENT DOCUMENTS

| | | | |
|---|---|---|---|
| 4,341,206 A | 7/1982 | Perrett et al. | |
| 4,710,075 A | 12/1987 | Davison | |
| 5,020,281 A | 6/1991 | Neff | |
| 5,540,696 A | 7/1996 | Booth, Jr. et al. | |
| 6,162,226 A | 12/2000 | DeCarlo, Jr. et al. | |
| 6,245,074 B1 | 6/2001 | Allard et al. | |
| 6,277,121 B1* | 8/2001 | Burkinshaw ....... | A61B 17/1677 606/80 |
| 6,712,823 B2 | 3/2004 | Grusin et al. | |
| 6,739,872 B1* | 5/2004 | Turri ..................... | A61B 17/16 433/75 |

(Continued)

FOREIGN PATENT DOCUMENTS

| | | |
|---|---|---|
| AU | 2015271829 | 12/2015 |
| CN | 103767759 | 5/2014 |

(Continued)

OTHER PUBLICATIONS

Video: Virtual Implant Positioning (VIP) System. Published to YouTube Feb. 22, 2018. Retrieved Nov. 22, 2019 from https://youtu.be/-x3IIHBBt9A.

(Continued)

*Primary Examiner* — Eric S Gibson
(74) *Attorney, Agent, or Firm* — Carlson, Gaskey & Olds, P.C.

(57) ABSTRACT

This disclosure relates to assemblies and methods for repairing bone defects. The assemblies disclosed herein may be utilized for determining a dimension of a surgical site and removing bone prior to positioning a graft and/or implant at the surgical site.

22 Claims, 21 Drawing Sheets

(56) References Cited

U.S. PATENT DOCUMENTS

| | | | |
|---|---|---|---|
| 6,884,246 B1 | 4/2005 | Sonnabend et al. | |
| 6,951,562 B2 * | 10/2005 | Zwirnmann | A61B 17/1633 606/80 |
| 7,141,074 B2 * | 11/2006 | Fanger | A61B 17/1617 606/80 |
| 7,163,542 B2 * | 1/2007 | Ryan | A61B 17/1617 606/96 |
| 7,326,215 B2 | 2/2008 | Myers et al. | |
| 7,503,921 B2 | 3/2009 | Berthusen et al. | |
| 7,527,631 B2 * | 5/2009 | Maroney | A61B 90/06 606/102 |
| 7,758,581 B2 | 7/2010 | Chervitz et al. | |
| 8,187,282 B2 | 5/2012 | Tornier et al. | |
| 9,198,732 B2 | 12/2015 | Iannotti et al. | |
| 9,358,029 B2 | 6/2016 | Sikora et al. | |
| 9,408,613 B2 | 8/2016 | Kehres et al. | |
| 9,561,040 B2 | 2/2017 | Winslow | |
| 9,615,839 B2 | 4/2017 | Olson | |
| 9,737,313 B1 | 8/2017 | Sohn et al. | |
| 9,839,436 B2 * | 12/2017 | Kehres | A61B 17/1778 |
| 9,839,438 B2 | 12/2017 | Eash | |
| 10,028,838 B2 | 7/2018 | Hodorek et al. | |
| 10,314,598 B2 | 6/2019 | Knape et al. | |
| 10,792,053 B2 * | 10/2020 | Asfora | A61B 17/1757 |
| 2003/0220646 A1 | 11/2003 | Thelen et al. | |
| 2004/0153080 A1 | 8/2004 | Dong et al. | |
| 2004/0267267 A1 | 12/2004 | Daniels et al. | |
| 2005/0059975 A1 * | 3/2005 | Fanger | A61B 17/1671 606/80 |
| 2005/0222571 A1 * | 10/2005 | Ryan | A61B 17/1617 606/80 |
| 2006/0004372 A1 * | 1/2006 | Zwirnmann | A61B 17/1633 606/80 |
| 2006/0074353 A1 | 4/2006 | Deffenbaugh et al. | |
| 2006/0184174 A1 * | 8/2006 | Harris, Jr. | A61B 17/1617 606/80 |
| 2007/0206996 A1 | 9/2007 | Bharadwaj et al. | |
| 2008/0009874 A1 | 1/2008 | Meridew et al. | |
| 2010/0076442 A1 | 3/2010 | Xie et al. | |
| 2011/0098710 A1 | 4/2011 | Spratt et al. | |
| 2013/0171585 A1 | 7/2013 | Huang | |
| 2014/0012389 A1 | 1/2014 | Ek | |
| 2014/0018810 A1 * | 1/2014 | Knape | A61B 17/1633 606/80 |
| 2015/0119891 A1 | 4/2015 | Goldberg et al. | |
| 2015/0190151 A1 | 7/2015 | Budhabhatti et al. | |
| 2015/0342620 A1 | 12/2015 | Winslow | |
| 2016/0045207 A1 | 2/2016 | Kovacs et al. | |
| 2016/0345987 A1 | 12/2016 | Guilloux et al. | |
| 2017/0303972 A1 * | 10/2017 | Schumacher | A61B 17/8811 |
| 2018/0008293 A1 | 1/2018 | Kovacs et al. | |
| 2018/0200068 A1 | 7/2018 | Goldberg et al. | |
| 2018/0303618 A1 | 10/2018 | Kovacs et al. | |
| 2018/0325687 A1 | 11/2018 | Deransart et al. | |
| 2019/0015118 A1 | 1/2019 | Neichel et al. | |
| 2019/0125371 A1 * | 5/2019 | Asfora | A61B 17/864 |
| 2019/0231369 A1 * | 8/2019 | Cardon | A61B 17/1684 |
| 2019/0269469 A1 * | 9/2019 | Bush, Jr. | A61B 34/20 |
| 2019/0290299 A1 | 9/2019 | Pacaccio et al. | |
| 2019/0358045 A1 * | 11/2019 | Boileau | A61F 2/4644 |
| 2021/0045754 A1 * | 2/2021 | Khosla | A61B 90/03 |

FOREIGN PATENT DOCUMENTS

| | | |
|---|---|---|
| CN | 104605913 | 5/2015 |
| DE | 3800482 | 7/1989 |
| DE | 102008053566 | 6/2009 |
| EP | 3206595 | 8/2017 |
| GB | 2281577 | 3/1995 |
| WO | 2015106136 | 7/2015 |
| WO | 2015187676 | 12/2015 |
| WO | 2017201262 | 11/2017 |

OTHER PUBLICATIONS

International Search Report for International Application No. PCT/US2021/012393 completed Apr. 14, 2021.

* cited by examiner

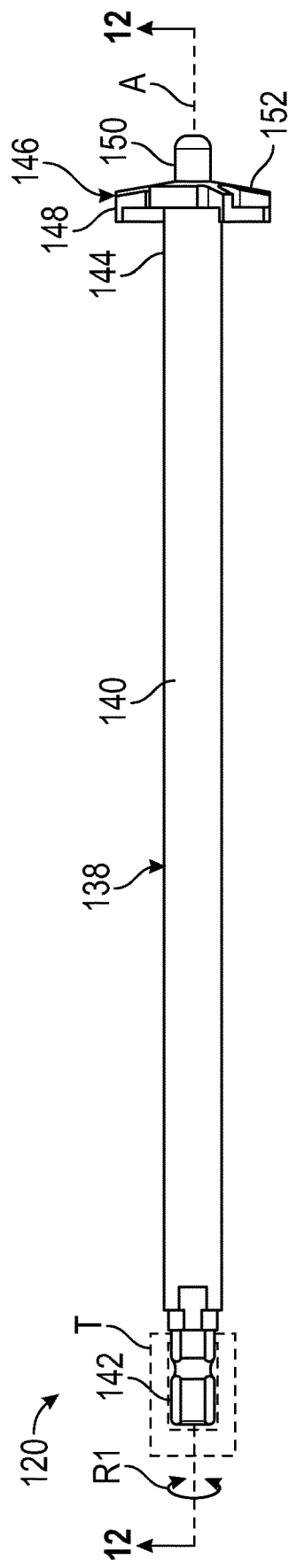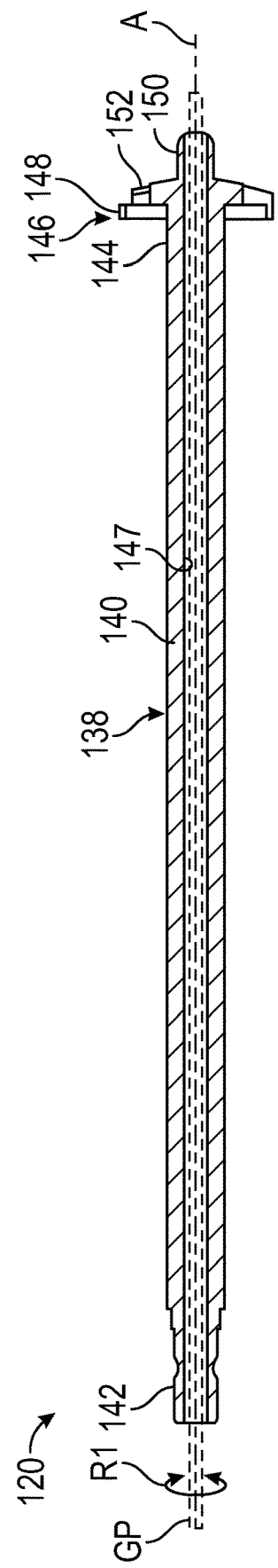
FIG. 11
FIG. 12

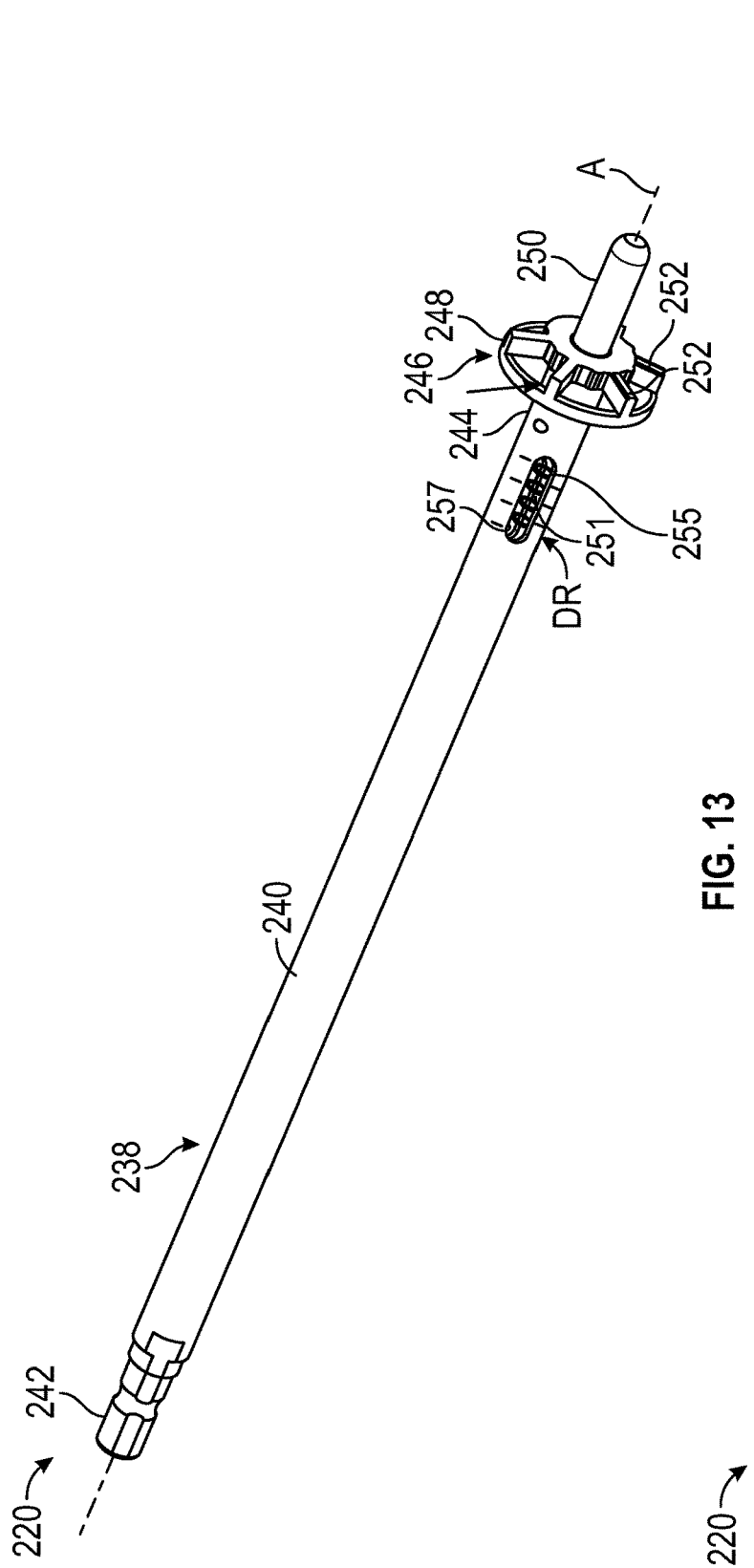
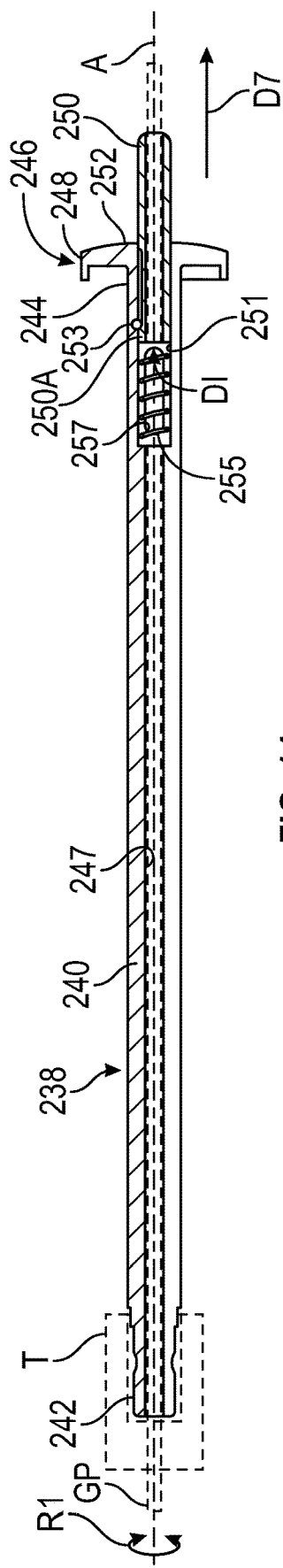
FIG. 13
FIG. 14

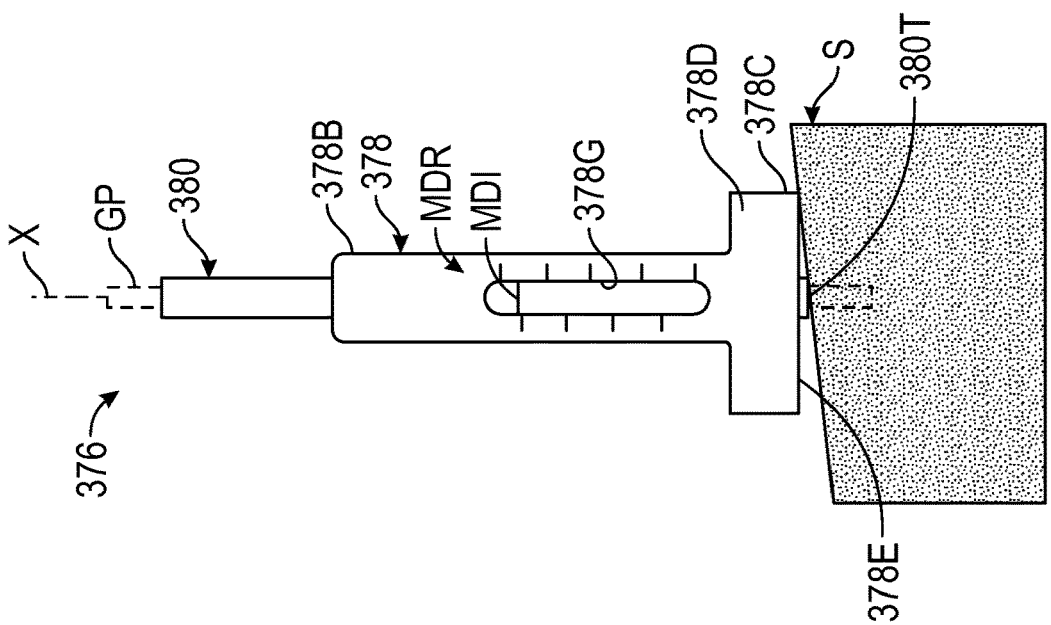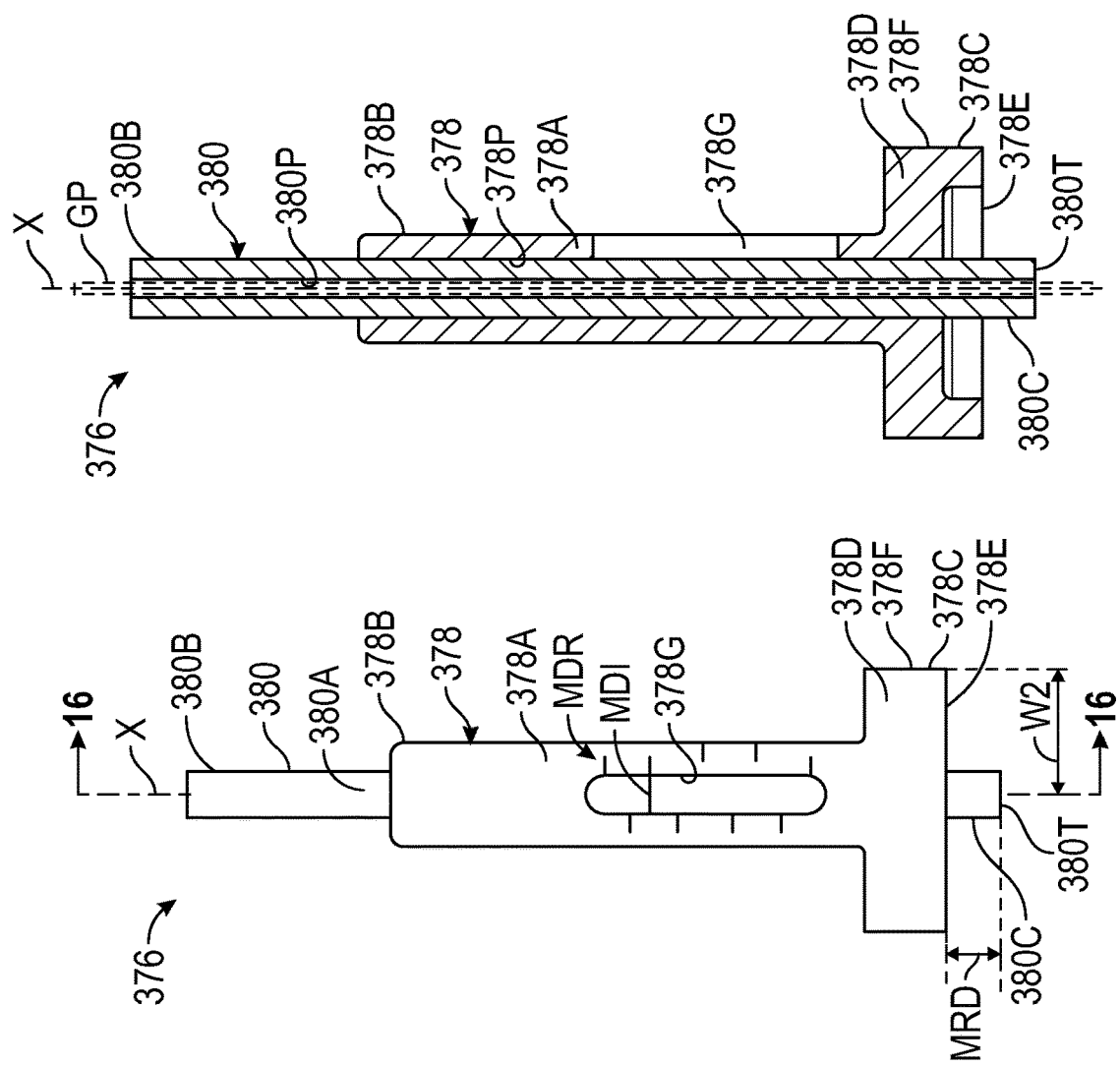

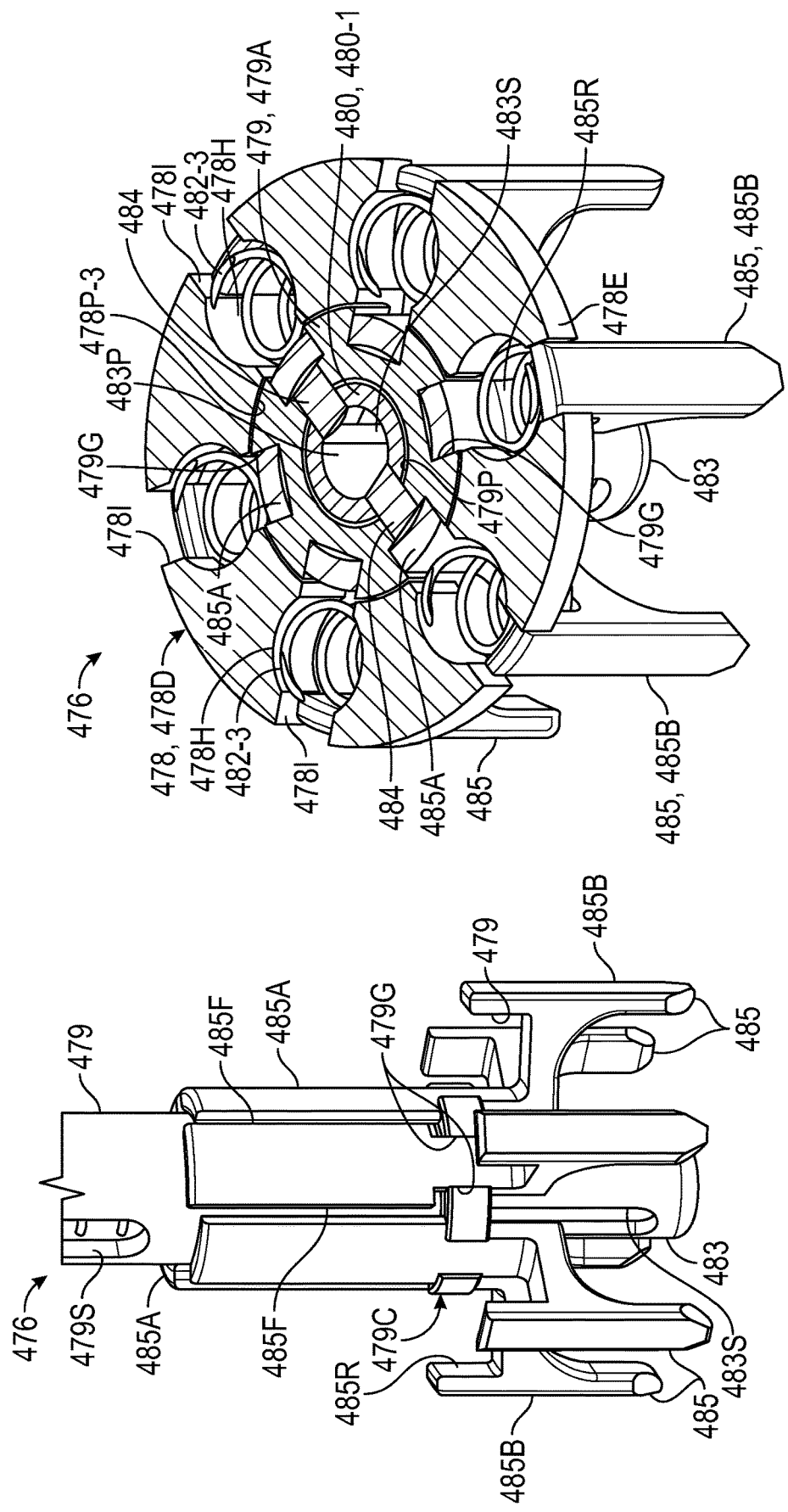

ASSEMBLIES FOR PREPARATION OF SURGICAL SITES

BACKGROUND

This disclosure relates to surgical devices and methods for repairing bone defects.

Many bones of the human musculoskeletal system include articular surfaces. The articular surfaces articulate relative to other bones to facilitate different types and degrees of joint movement. The articular surfaces can erode (i.e., experience bone loss) over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to a fill defect in the glenoid bone. A reamer may be utilized to form a recess in the bone dimensioned to receive the bone graft or implant.

SUMMARY

This disclosure relates to surgical devices and methods. The surgical devices may be used during methods for repairing bone defects. The surgical devices described herein may be utilized to form a recess or otherwise shape a surface at a surgical site.

A reaming assembly for preparation of a surgical site according to an embodiment of the present disclosure includes, inter alia, a housing including a housing body extending along a longitudinal axis between a proximal end portion and a distal end portion, a passageway extending along the longitudinal axis, and a hood extending radially outwardly from the housing body along the distal end portion. A rotatable drive shaft is received in the passageway. A reaming head includes cutting teeth. The reaming head is coupled to the drive shaft such that the hood is moveable to at least partially surround the cutting teeth. A lock mechanism includes a micro lock member and a macro lock member that cooperate to establish at least a locked mode and a micro adjustment mode. The macro lock member includes lock threading engageable with shaft threading along the drive shaft such that the reaming head translates along the longitudinal axis in response to relative rotation between the housing and the drive shaft in the micro adjustment mode. The micro lock member is disengageable with the drive shaft to permit relative rotation between the housing and the drive shaft in the micro adjustment mode. The micro lock member is engageable with the drive shaft to block relative rotation between the housing and the drive shaft in the locked mode.

A kit for preparation of a surgical site according to an embodiment of the present disclosure includes, inter alia, a reaming assembly including a housing having a housing body extending along a first longitudinal axis between a proximal end portion and a distal end portion, a reaming cavity extending inwardly from a terminal end of the distal end portion, a passageway extending along the first longitudinal axis between the proximal end portion and the reaming cavity, and a carrier slot extending across the passageway. A rotatable drive shaft is received in the passageway. The drive shaft includes shaft threading. A reaming head is coupled to the drive shaft, and the reaming head includes cutting teeth at least partially received in the reaming cavity. A lock mechanism includes a macro switch and a micro switch configured to set a reaming depth of a range of reaming depths established between the reaming head and the housing. The macro switch includes a lock cavity and lock threading extending along a shaft passage. The macro switch is slidably received in the carrier slot, the micro switch is slidably received in the lock cavity such that the micro switch selectively engages the drive shaft to limit relative rotation, and the drive shaft is slidably received in the shaft passage such that the lock threading selectively engages the shaft threading.

A method of preparing a surgical site in bone according to an embodiment of the present disclosure includes, inter alia, setting a lock mechanism in a micro adjustment mode, translating a reaming head relative to a distal end of a housing to set a reaming depth in response to relative rotation between the housing and the reaming head in the micro adjustment mode, and setting the lock mechanism in a locked mode to block relative rotation between the housing and the reaming head.

BRIEF DESCRIPTION OF THE DRAWINGS

FIG. 11 illustrates a side view of an exemplary reaming assembly for preparing a surgical site according to another embodiment.

FIG. 12 illustrates a sectional view of the assembly taken along line 12-12 of FIG. 11.

FIG. 13 illustrates a perspective view of an exemplary reaming assembly for preparing a surgical site according to yet another embodiment.

FIG. 14 illustrates a sectional view of the assembly of FIG. 13.

FIG. 15 illustrates a side view of an exemplary depth gauge instrument for evaluating a surgical site.

FIG. 16 illustrates a sectional view of the depth gauge instrument taken along line 16-16 of FIG. 15.

FIG. 17 illustrates a side view of the depth gauge instrument of FIG. 15 including a control member positioned relative to a surgical site.

FIG. 23B illustrates an isolated perspective view of selected portions of the depth gauge instrument of FIG. 23A.

FIG. 23C illustrates a sectional view of the depth gauge instrument along line 23C-23C of FIG. 23A.

DETAILED DESCRIPTION

Figure 1:
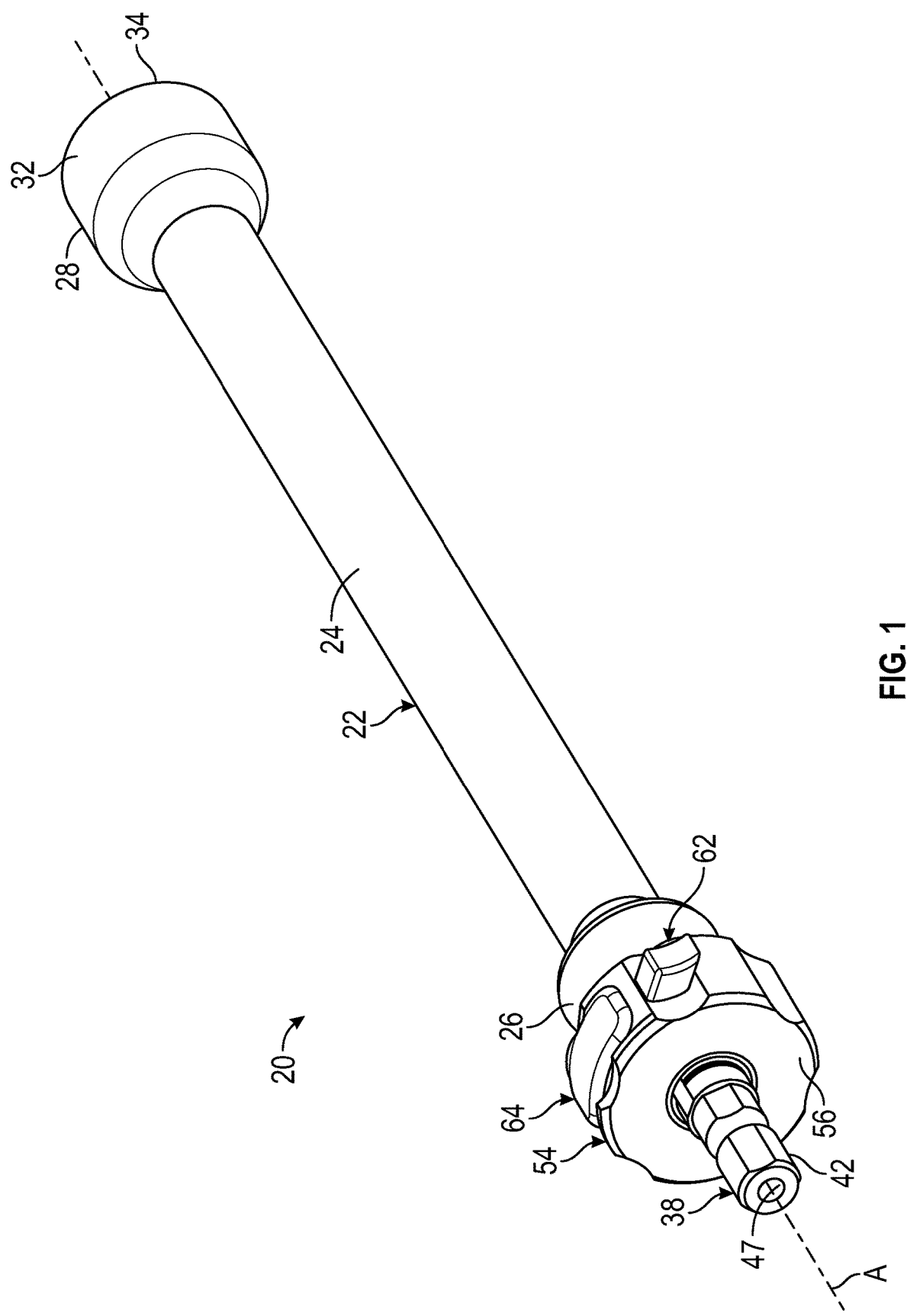
FIG. 1 illustrates a perspective view of an exemplary reaming assembly for preparing a surgical site.

This disclosure relates to surgical devices and methods for repairing bone defects. The devices described herein may be capable of dimensioning or otherwise preparing a defect surface at a surgical site, including reaming bone or other tissue. The disclosed surgical devices include reaming assemblies having an adjustable stop sleeve or hood dimensioned to contact bone or other tissue at a surgical site. The adjustable hood can be utilized in combination with a locking mechanism including micro depth and/or macro depth adjustment features that provide different granularity of adjustments to a reaming depth. The disclosed devices can provide an improved depth control during a reaming operation.

A reaming assembly for preparation of a surgical site according to an exemplary aspect of the present disclosure includes, inter alia, a housing including a housing body extending along a longitudinal axis between a proximal end portion and a distal end portion, a passageway extending along the longitudinal axis, and a hood extending radially outwardly from the housing body along the distal end portion. A rotatable drive shaft is received in the passageway. A reaming head includes cutting teeth. The reaming head is coupled to the drive shaft such that the hood is moveable to at least partially surround the cutting teeth. A lock mechanism includes a micro lock member and a macro lock member that cooperate to establish at least a locked mode and a micro adjustment mode. The macro lock member includes lock threading engageable with shaft threading along the drive shaft such that the reaming head translates along the longitudinal axis in response to relative rotation between the housing and the drive shaft in the micro adjustment mode. The micro lock member is disengageable with the drive shaft to permit relative rotation between the housing and the drive shaft in the micro adjustment mode. The micro lock member is engageable with the drive shaft to block relative rotation between the housing and the drive shaft in the locked mode.

In a further embodiment, the reaming head includes a reaming portion extending outwardly from a nose portion, and the cutting teeth extend along both the reaming and nose portions.

In a further embodiment, the hood is dimensioned to surround a portion of the cutting teeth along the reaming portion, and the nose portion is dimensioned to extend outwardly from the hood in response to translation of the reaming head along the longitudinal axis in at least the micro adjustment mode.

In a further embodiment, the micro lock member and the macro lock member cooperate to establish a macro adjustment mode, and the macro lock member is moveable to cause the lock threading to disengage the shaft threading such that the reaming head translates along the longitudinal axis in response to sliding the housing along a length of the drive shaft in the macro adjustment mode.

In a further embodiment, the macro lock member includes a carrier body having a shaft passage and a lock cavity, the lock threading extends along the shaft passage, the drive shaft is slidably received in the shaft passage such that the shaft threading faces the lock threading, and the micro lock member includes a lock body slidably received in the lock cavity.

In a further embodiment, the lock body includes a flat portion dimensioned to engage a flat portion along the drive shaft in the micro adjustment and locked modes, and the flat portion of the drive shaft extends across a length of the shaft threading.

In a further embodiment, reaming assembly includes a first spring member between the housing and the carrier body, the housing includes a carrier slot dimensioned to slidably receive the carrier body, and the first spring member is dimensioned to bias the lock threading into engagement with the shaft threading in the micro adjustment and locked modes.

In a further embodiment, reaming assembly includes a retention member slidably received in a retention cavity of the carrier body, the retention member engages a first recess of the lock body to set a first position of the lock body in the micro adjustment mode, and the retention member engages a second recess of the lock body to set a second position of the lock body in the macro adjustment and locked modes.

A kit for preparation of a surgical site according to an exemplary aspect of the present disclosure includes, inter alia, a reaming assembly including a housing having a housing body extending along a first longitudinal axis between a proximal end portion and a distal end portion, a reaming cavity extending inwardly from a terminal end of the distal end portion, a passageway extending along the first longitudinal axis between the proximal end portion and the reaming cavity, and a carrier slot extending across the passageway. A rotatable drive shaft is received in the passageway. The drive shaft includes shaft threading. A reaming head is coupled to the drive shaft, and the reaming head includes cutting teeth at least partially received in the reaming cavity. A lock mechanism includes a macro switch and a micro switch configured to set a reaming depth of a range of reaming depths established between the reaming head and the housing. The macro switch includes a lock cavity and lock threading extending along a shaft passage. The macro switch is slidably received in the carrier slot, the micro switch is slidably received in the lock cavity such that the micro switch selectively engages the drive shaft to limit relative rotation, and the drive shaft is slidably received in the shaft passage such that the lock threading selectively engages the shaft threading.

In a further embodiment, the macro switch and the micro switch cooperate to establish at least a micro adjustment mode and a macro adjustment mode, the lock threading engages the shaft threading such that the reaming head translates along the first longitudinal axis in response to relative rotation between the lock threading and the shaft threading in the micro adjustment mode, and the lock threading disengages the shaft threading such that the reaming head translates along the first longitudinal axis in response to sliding the housing along a length of the drive shaft in the macro adjustment mode.

In a further embodiment, the macro switch and the micro switch cooperate to establish a locked mode, the drive shaft includes an interruption extending across the shaft threading, and the micro switch is dimensioned to disengage the interruption in the macro adjustment mode and is dimensioned to engage the interruption to block relative rotation between the housing and the drive shaft in the locked mode.

In a further embodiment, the macro switch and the micro switch cooperate to establish a locked mode, the micro switch disengages the drive shaft to permit relative rotation between the housing and the drive shaft in the micro adjustment mode, the micro switch engages the drive shaft to block relative rotation between the housing and the drive shaft in the locked mode, the macro switch includes a retention cavity dimensioned to slidably receive a retention member, the retention member is dimensioned to set a first position of the micro switch in the micro adjustment mode, and the retention member is dimensioned to set a second position of the micro switch in the macro adjustment and locked modes.

In a further embodiment, the kit includes a depth gauge for determining a dimension of a surgical site. The depth gauge includes a gauge housing extending along a second longitudinal axis between proximal and distal end portions of the gauge housing, a depth indicator aligned with a depth ruler, the depth ruler dimensioned with respect to the range of reaming depths of the reaming head, and at least one control member extending outwardly from the distal end portion of the gauge housing. The depth indicator is moveable relative to a depth ruler in response to relative movement between the at least one control member relative to the gauge housing.

In a further embodiment, the depth gauge includes an actuation shaft extending along the second longitudinal axis, the at least one control member includes an array of control legs outwardly biased relative to the distal end portion of the gauge housing, and the actuation shaft is configured to set a position of the depth indicator relative to the depth ruler based on a longitudinally outermost position of the array of control legs relative to the second longitudinal axis.

A method of preparing a surgical site in bone according to an exemplary aspect of the present disclosure includes, inter alia, setting a lock mechanism in a micro adjustment mode, translating a reaming head relative to a distal end of a housing to set a reaming depth in response to relative rotation between the housing and the reaming head in the micro adjustment mode, and setting the lock mechanism in a locked mode to block relative rotation between the housing and the reaming head.

In a further embodiment, the reaming head includes a reaming portion extending outwardly from a nose portion, cutting teeth extend about both the reaming and nose portions, the housing includes a hood dimensioned to surround a portion of the cutting teeth at the distal end, and the translating step includes moving the portion of the cutting teeth relative to the hood in the micro adjustment mode.

In a further embodiment, the reaming head is coupled to a cannulated drive shaft including an inner bore. The method includes positioning a guide pin at least partially in the inner bore, and rotating the reaming head about the guide pin to remove bone along the surgical site.

In a further embodiment, the reaming head is coupled to a drive shaft, the lock mechanism includes a macro switch and a micro switch, and the step of setting the lock mechanism in the micro adjustment mode includes moving lock threading of the macro switch into engagement with shaft threading of the drive shaft and includes sliding the micro switch across the macro switch such that the micro switch disengages the drive shaft.

In a further embodiment, the step of setting the lock mechanism in the locked mode includes sliding the micro switch across the macro switch such that the micro switch engages the drive shaft.

In a further embodiment, the method includes setting the lock mechanism in a macro adjustment mode, including moving the macro switch such that the lock threading disengages with the shaft threading, and translating the reaming head relative to the distal end of the housing in response to sliding the housing along the drive shaft in the macro adjustment mode.

In a further embodiment, the method includes selecting the reaming depth based on a geometry of the housing and a profile of the surgical site.

In a further embodiment, the step of selecting the reaming depth includes positioning a depth gauge relative to the surgical site, moving a control member relative to a gauge housing of the depth gauge in response to the control member contacting a surface along the surgical site, and setting a position of a depth indicator relative to a depth ruler based on a position of the control member, the reaming depth based on the position of the depth indicator.

FIGS. 1-10 illustrate an exemplary reaming assembly that can be utilized for various surgical procedures, such as for preparation of a surgical site. For example, the reaming assembly 20 may be utilized in a shoulder reconstruction to remove bone along an articulating surface of a glenoid or humeral head. The bone may be removed from a defect in the articulating surface.

Figure 2:
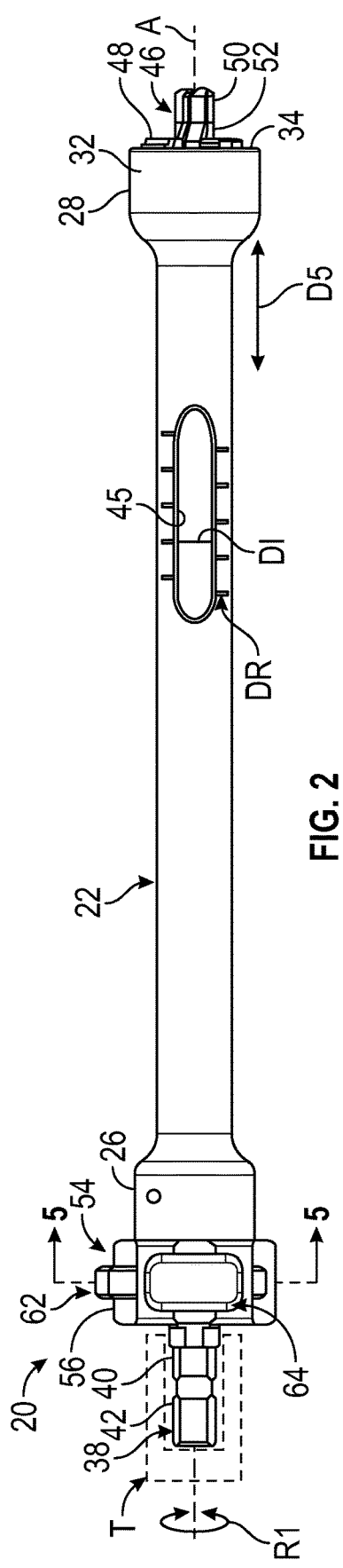
FIG. 2 illustrates a side view of the assembly of FIG. 1.
Figure 3:
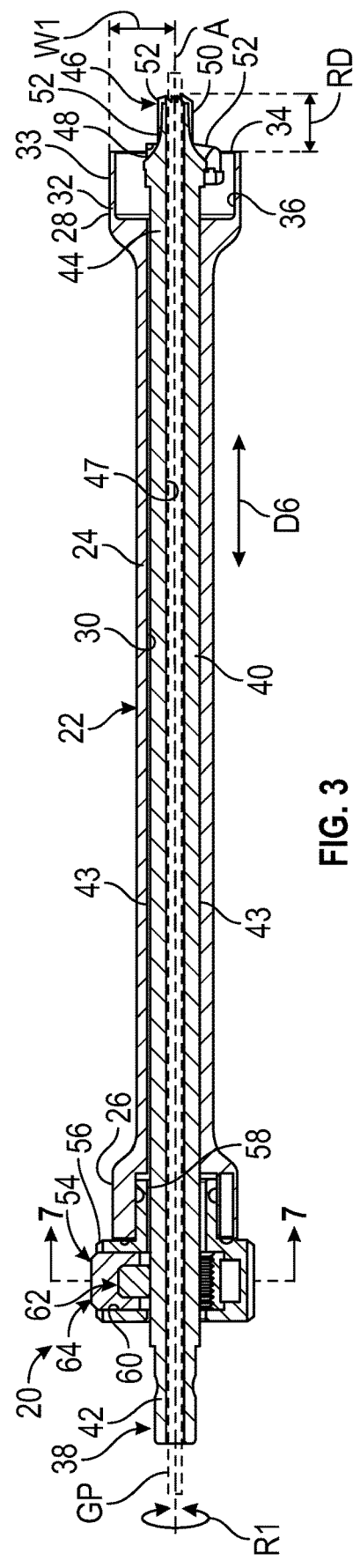
FIG. 3 illustrates a sectional view of the assembly of FIG. 1.

Referring to FIGS. 1-3, the reaming assembly 20 includes a housing 22 including a housing body 24 extending along a longitudinal axis A between a proximal end portion 26 and a distal end portion 28. The housing body 24 can have a generally tubular geometry. A housing passageway 30 (FIG. 3) extends along a longitudinal axis A between the proximal end portion 26 and distal end portion 28.

The housing 22 includes an adjustable stop sleeve or hood 32 extending radially outwardly from the housing body 24 along the distal end portion 28. The hood 32 has a generally bell-shaped geometry and defines a terminal end 34 of the housing 22. The hood 32 is dimensioned to contact or abut tissue such as bone along the terminal end 34 to limit a reaming depth of the assembly 20. The housing 22 includes a reaming cavity 36 (FIG. 3) extending inwardly from the terminal end 34. The passageway 30 extends along the longitudinal axis A between the proximal end portion 26 and the reaming cavity 36, as illustrated by FIG. 3.

Figure 4:
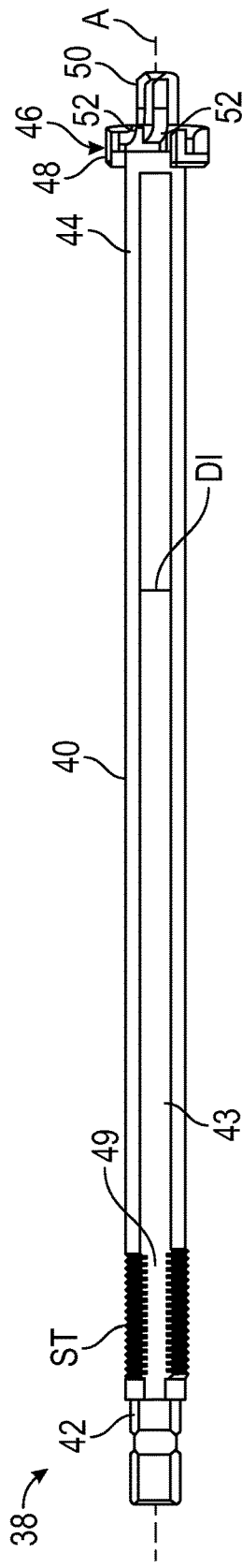
FIG. 4 illustrates an isolated side view of a drive shaft of the assembly of FIG. 1.

Referring to FIGS. 2-4, with continuing reference to FIG. 1, the reaming assembly 20 includes a rotatable drive shaft 38 at least partially received in the passageway 30 and reaming cavity 36. An isolated view of the drive shaft 38 is disclosed in FIG. 4. The drive shaft 38 includes an elongated shaft body 40 extending between a proximal end portion 42 and a distal end portion 44 (FIGS. 3-4) along the longitudinal axis A. The proximal end portion 42 of the drive shaft 38 can be coupled to tooling T (shown in dashed lines in FIG. 2 for illustrative purposes) to rotate the drive shaft 38 in a rotational direction R1 (FIG. 3) about the longitudinal axis A.

The reaming assembly 20 includes a reaming head 46 coupled to the distal end portion 44 of the drive shaft 38. The reaming head 46 includes a reaming portion 48 extending radially outwardly from a nose portion 50. The reaming head 46 includes cutting (or reaming) teeth 52 extending along both reaming portion 48 and the nose portion 50. The cutting teeth 52 are rotatable in the rotational direction R1 (FIG. 3) about the longitudinal axis A to remove bone or other tissue from a surgical site. The cutting teeth 52 are at least partially received in the reaming cavity 36, as illustrated in FIG. 3. The hood 32 is dimensioned to surround a portion of the cutting teeth 52 along the reaming portion 48, as illustrated in FIGS. 2-3. In embodiments, the hood 32 is moveable to surround a portion of the cutting teeth 52 along the reaming and nose portions 48, 50 (see, e.g., FIGS. 3 and 16).

In the illustrative embodiment of FIG. 2, the reaming assembly 20 includes at least one elongated viewing window 45 along a sidewall of the housing 22. The reaming assembly 20 includes a depth ruler DR and a depth indicator DI (see also FIG. 4) moveable relative to each other. The depth indicator DI is axially aligned with a selected value along the depth ruler DR relative to the longitudinal axis A. The depth ruler DR can correspond to a range of depths of a hole or recess to be formed in a surgical site. The depth ruler DR can include circumferential markings on a periphery of the housing 22, for example. In embodiments, alignment of the depth indicator DI and a selected value along the depth ruler DR corresponds to a reaming depth RD (FIG. 3). The reaming depth RD can be defined as a distance between a distal end of the reaming head 46 and the terminal end 34 of the reaming assembly 20 along the hood 32.

Referring to FIGS. 3-4, with continuing reference to FIGS. 1-2, the drive shaft 38 has a generally cylindrical geometry. The drive shaft 38 includes one or more flat portions (or engagement faces) 43 that extend along a length of the shaft body 40 between the proximal and distal end portions 42, 44. In the illustrated embodiment of FIG. 3, the drive shaft 38 includes opposed flat portions 43 that extend substantially along the length of the shaft body 40. Each of the flat portions 43 can have a substantially flat or planar geometry.

As illustrated in FIG. 4, the drive shaft 38 includes shaft threading ST extending about a circumference of the shaft body 40. The flat portion 43 of the drive shaft 38 includes an interface 49. The interface 49 establishes an interruption extending across a length of the shaft threading ST such that the shaft threading ST is discontinuous.

In the illustrative embodiment of FIG. 3, the drive shaft 38 is cannulated drive shaft including an inner bore 47 dimensioned to extend along the longitudinal axis A (see also FIG. 1). The inner bore 47 can be dimensioned to at least partially receive a guide pin GP (shown in dashed lines for illustrative purposes). The guide pin GP can be secured in a surgical site. The reaming assembly 20 can be translated along the guide pin GP to engage surfaces of the surgical site at a selected location and/or orientation.

Referring to FIGS. 2-3, with continuing reference to FIG. 1, the reaming assembly 20 includes a lock mechanism 54 having macro and micro depth adjustment features for setting the reaming depth RD. The lock mechanism 54 includes a dial or lock body 56. The lock body 56 forms a portion of the housing 22. The lock body 56 is fixedly attached or otherwise secured to the housing body 24 along the proximal end portion 26. In other embodiments, the lock body 56 is integrally formed with the housing body 24. The lock body 56 includes a lock passageway 58 dimensioned to receive a portion of the drive shaft 38, as illustrated in FIG. 3. The lock passageway 58 is dimensioned to extend from the housing passageway 30 along the longitudinal axis A. The lock body 56 includes a carrier slot 60 transverse to and extending across the lock passageway 58.

The lock mechanism 54 includes a micro lock member 62 and a macro lock member 64 that cooperate to establish a plurality of modes of the lock mechanism 54, including at least a locked (or first) mode, a micro adjustment (or second) mode, and a macro adjustment (or third) mode. The locked mechanism 54 is configured such that relative movement between the housing 22 and drive shaft 38 is blocked or otherwise limited in the lock mode. The lock mechanism 54 is configured such that relatively small adjustments between the relative position of the housing 22 and drive shaft 38 can be made in the micro adjustment mode and relatively larger adjustments can be made in the macro adjustment mode. In other embodiments, the lock mechanism 54 includes only a locked mode and one of the micro and macro adjustment modes.

Figure 5:
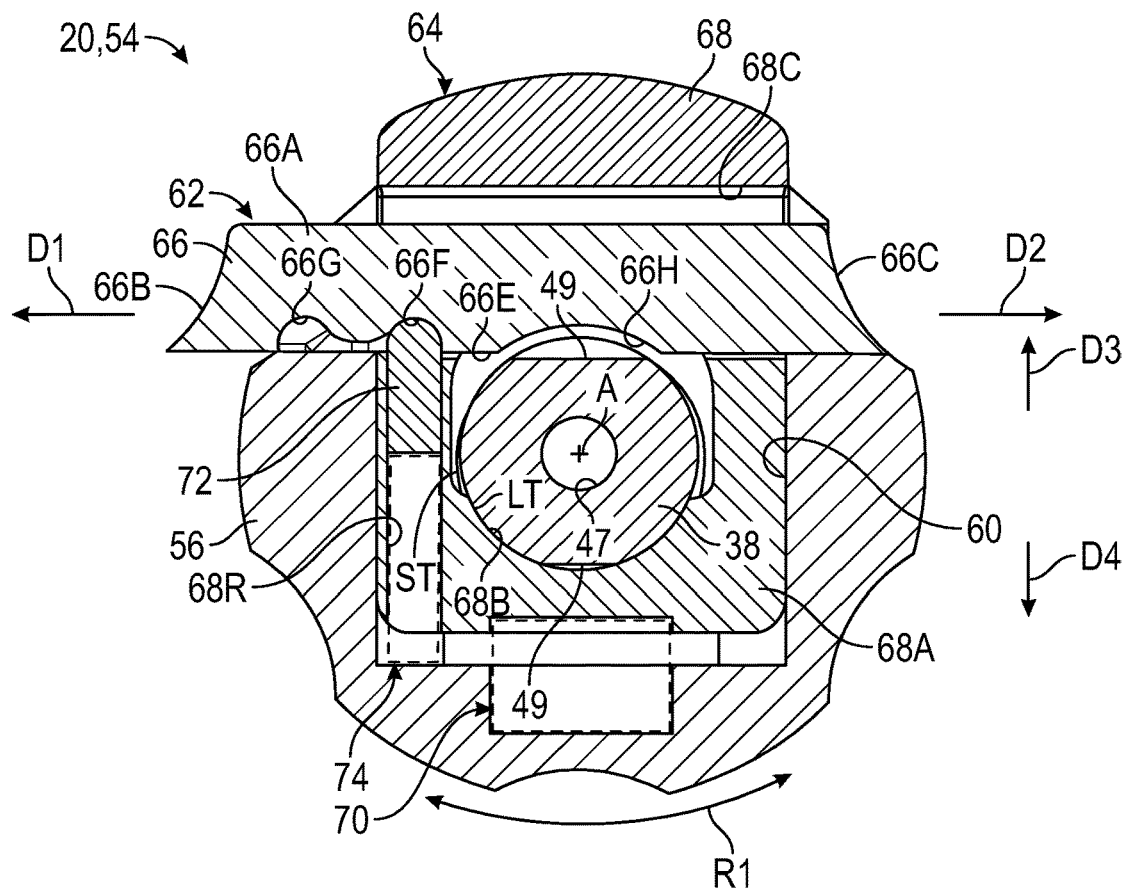
FIG. 5 illustrates a sectional view of a lock mechanism taken along line 5-5 of FIG. 2 in a micro adjustment mode.
Figure 6:
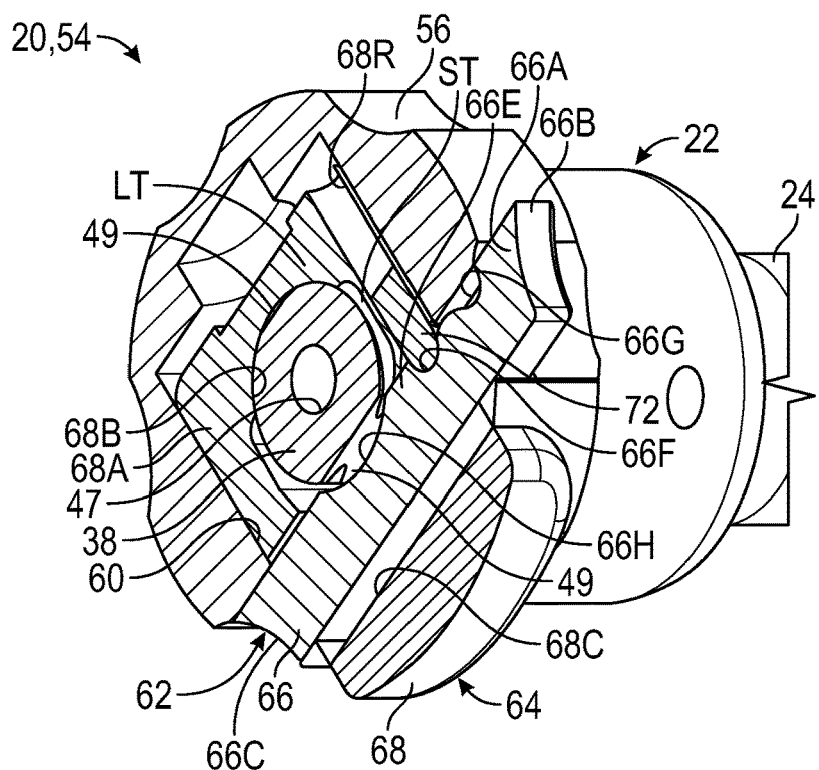
FIG. 6 illustrates a perspective view of the lock mechanism of FIG. 5.

Referring to FIGS. 5-6, with continuing reference to FIGS. 2-3, the lock mechanism 54 is illustrated in the micro adjustment mode. The micro lock member 62 includes a micro switch 66. The macro lock member 64 includes a macro switch 68. The switches 66, 68 can be toggled between first and second positions to set the modes of the lock mechanism 54. The macro switch 68 includes a carrier body 68A having a shaft passage 68B and a lock cavity 68C. The carrier slot 60 is dimensioned to slidably receive at least a portion of the carrier body 68A. The macro switch 68 includes lock threading LT that extends along a periphery of the shaft passage 68B (see also FIG. 9). The drive shaft 38 is slidably received in the shaft passage 68B such that the shaft threading ST faces and selectively engages the lock threading LT, as illustrated by FIGS. 5-6 (see also FIG. 8).

Figure 7:
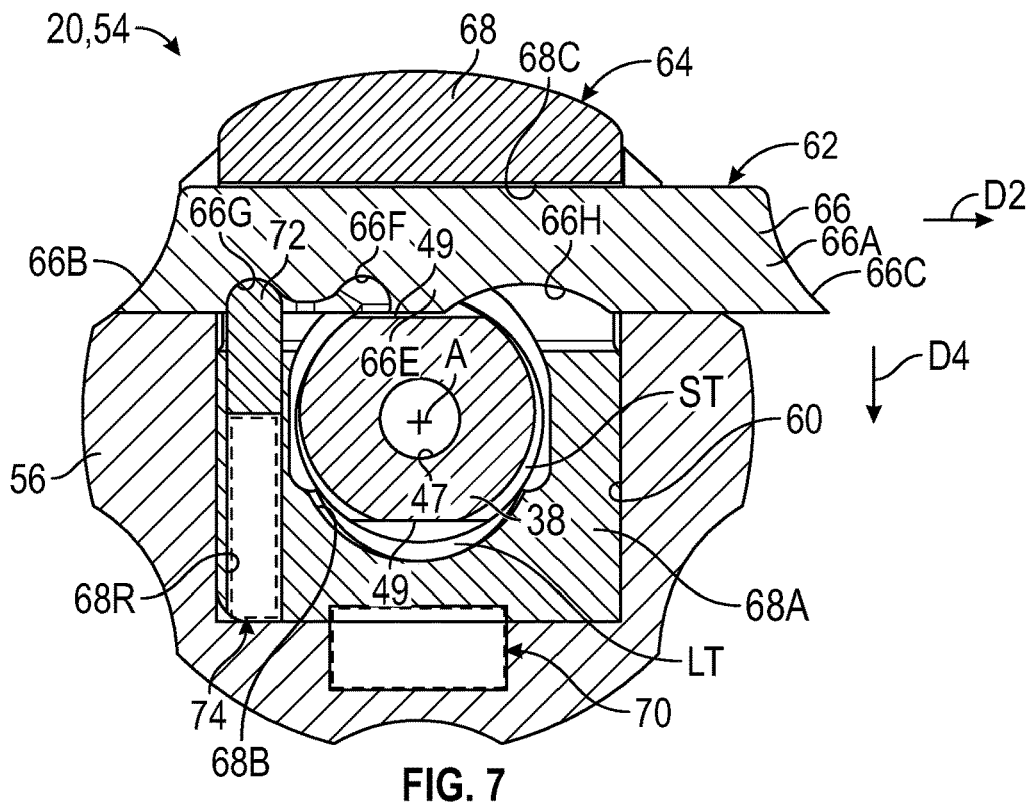
FIG. 7 illustrates a sectional view of the lock mechanism taken along line 7-7 of FIG. 3 in a macro adjustment mode.
Figure 10:
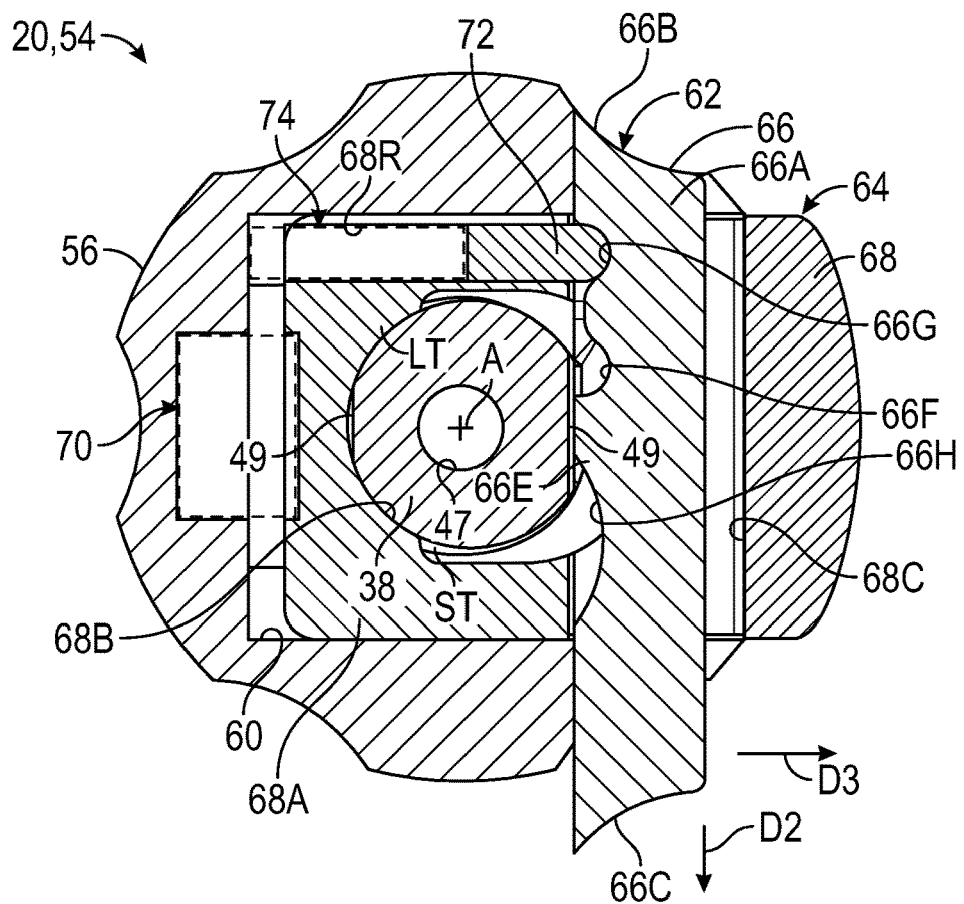
FIG. 10 illustrates a sectional view of the lock mechanism of the assembly of FIG. 1 in a locked mode.

The lock mechanism 54 includes a first spring member 70 and a second spring member 74 (shown in dashed lines in FIGS. 5, 7 and 10 for illustrative purposes). Various spring configurations can be utilized for the spring members 70, 74, including helical compression springs, conical springs, clock springs, torsion springs, plate springs, and extension springs.

The first spring member 70 is dimensioned to extend between the lock body 56 and the carrier body 68A. The first spring member 70 is dimensioned to bias or urge the lock threading LT into engagement with the shaft threading ST in the micro adjustment mode (see FIG. 5) and in the locked mode (see FIG. 7).

The micro switch 66 is dimensioned to disengage each interface 49 of the drive shaft 38 to permit relative rotation between the housing 22 and drive shaft 38 in the micro adjustment mode, and is dimensioned to engage one of the interfaces 49 to block or otherwise limit relative rotation between the housing 22 and drive shaft 38 in the locked mode. The micro switch 66 includes a lock body 66A extending between a first end 66B and a second, opposed end 66C. The lock body 66A is slidably received in the lock cavity 68C of the macro switch 68 such that the micro switch 66 selectively engages the drive shaft 38 to limit relative rotation. The lock body 66A includes an engagement (or flat)

portion 66E dimensioned to engage one of the interfaces 49 in the micro adjustment and lock modes. The engagement portion 66E and interfaces 49 can have a complementary geometry. In the illustrated embodiment of FIGS. 5-6, the engagement portion 66E has a substantially flat or planar geometry. In other embodiments, the engagement portion 66E is dimensioned to interfit with one or more depressions or grooves along the drive shaft 38.

The lock body 66A of the micro switch 66 includes a first recess 66F, a second recess 66G and a shaft (or third) recess 66H. The first recess 66F is between the second recess 66G and shaft recess 66H. The engagement portion 66E extends between the first recess 66F and shaft recess 66H. The recesses 66F, 66G and 66H can have a generally arcuate geometry, for example. The shaft recess 66H has a complementary geometry with the circumference of the shaft body 40 of the drive shaft 38.

The lock mechanism 54 includes a retention member 72 slidably received in a retention cavity 68R of the carrier body 68A. In the illustrative embodiment of FIGS. 5-6, the retention member 72 is an elongated retention pin. The retention member 72 includes an end having a complementary geometry with surfaces of the first and second recesses 66F, 66G. The retention member 72 is dimensioned to set a first position (see FIG. 5) of the micro switch 66 in the micro adjustment mode and is dimensioned to set a second position (see FIGS. 7 and 10) of the micro switch 66 in the macro adjustment and lock modes.

The second spring member 74 is dimensioned to extend along the retention cavity 68R between the retention member 72 and a wall of the lock body 56. The second spring member 74 is dimensioned to bias or urge the retention member 72 into engagement with the lock body 66A along a selected one of the first and second recesses 66F, 66G.

Figure 8:
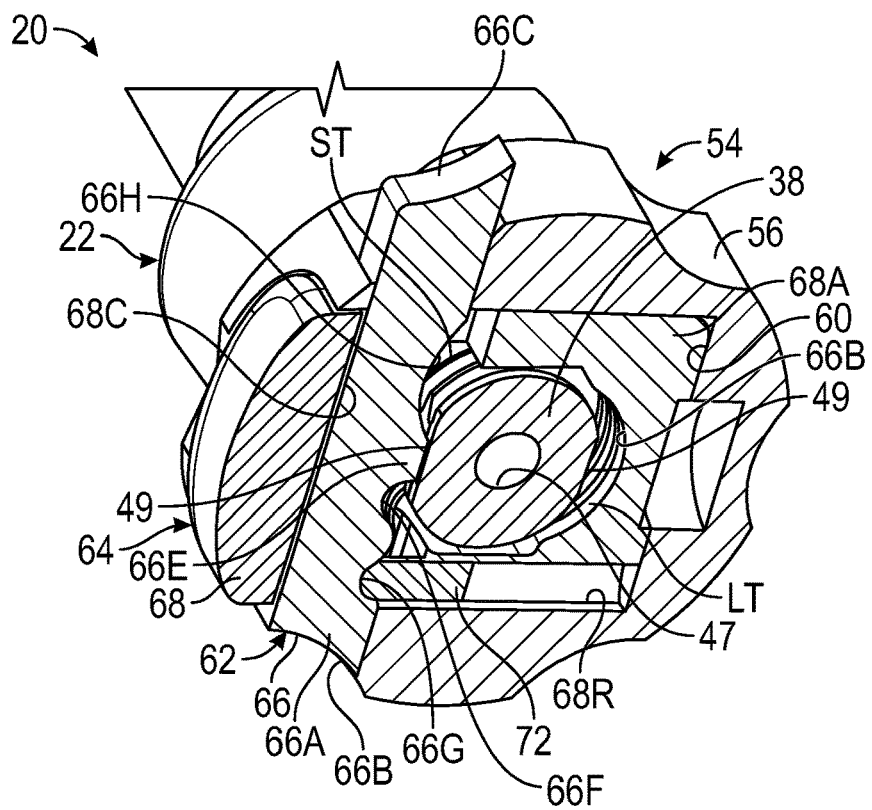
FIG. 8 illustrates a perspective view of the lock mechanism of FIG. 7.

The micro switch 66 is moveable in a first direction D1 to set the first position of the micro switch 66 and in a second, opposed direction D2 to set a second position of the micro switch 66 (see FIG. 5). Movement of the micro switch 66 in the first direction D1 causes the retention member 72 to engage the first recess 66F of the lock body 66A to set the first position of the micro switch 66 in the micro adjustment mode. Movement of the micro switch 66 in the second direction D2 causes the retention member 72 to engage the second recess 66G of the lock body 66A to set the second position of the micro switch 66 in the macro adjustment mode as illustrated in FIGS. 7-8, and in the locked mode as illustrated in FIG. 10. A surgeon or operator can apply a force to the micro switch 66 in the directions D1 or D2 to overcome a bias force of the second spring member 74, causing the retention member 72 to engage with another one of the first and second recesses 66F, 66G.

The macro switch 68 is moveable in a third direction D3 to set a first position of the macro switch 68 (see FIGS. 5 and 10) and a fourth, opposed direction D4 to set a second position of the macro switch 68 (see FIG. 7).

The first spring member 70 is dimensioned to bias the carrier body 68A in the third direction D3. An operator can apply a force to the macro switch 68 in the direction D4 to overcome a bias force of the first spring member 70.

In the micro adjustment mode of FIGS. 5-6, the lock threading LT engages with the shaft threading ST such that the reaming head 46 translates in an axial direction D5 (FIG. 2) along the longitudinal axis A in response to relative rotation in the rotational direction R1 (FIGS. 2 and 5) between the housing 22 and drive shaft 38. The nose portion 50 of the reaming head 46 is dimensioned to extend outwardly from the hood 32 in response to translation of the reaming head 46 in the direction D5 along the longitudinal axis A.

The micro switch 66 is moveable in the direction D1 to the first position such that the shaft recess 66H is circumferentially aligned with the outer diameter of the drive shaft 38 in the micro adjustment mode. The engagement portion 66E of the micro switch 66 is disengaged with each interface 49 of the drive shaft 38 to permit relative rotation between the housing 22 and drive shaft 38. The relative rotation between the lock threading LT and shaft threading ST causes the drive shaft 38 to translate along the longitudinal axis A. The reaming head 46 is coupled to the drive shaft 38 such that relative movement between the hood 32 and drive shaft 38 can cause the hood 32 to at least partially surround the cutting teeth 52 (see, e.g., FIGS. 2 and 16-17).

Figure 9:
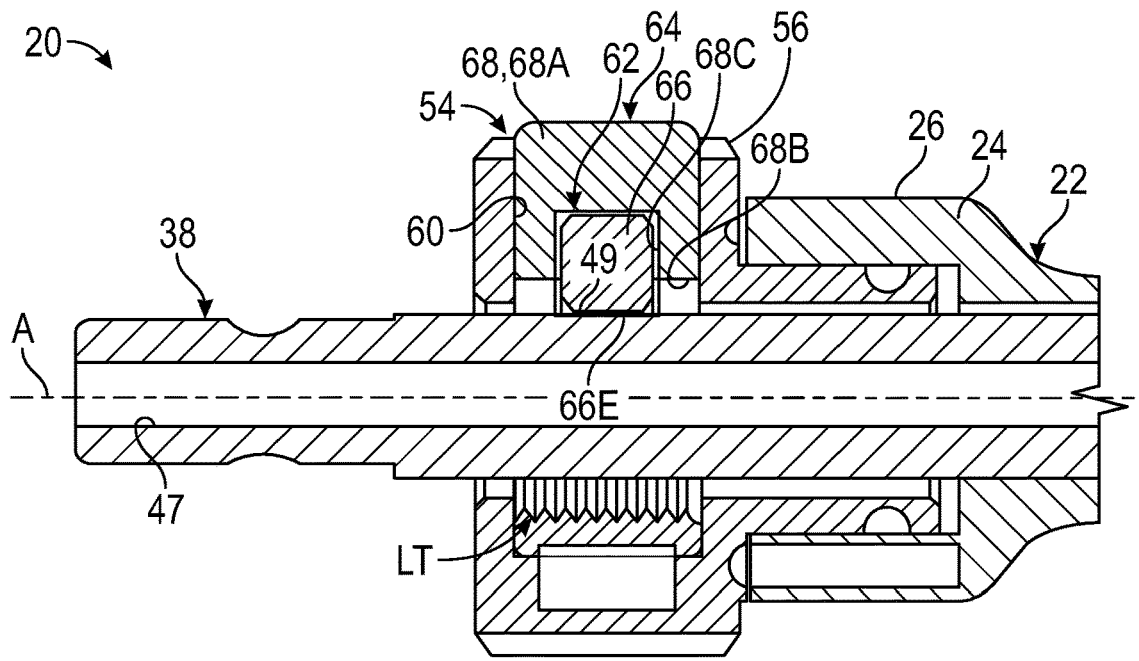
FIG. 9 illustrates selected portions of the lock mechanism of FIG. 3 in the macro adjustment mode.

Referring to FIGS. 7-9, with continuing reference to FIGS. 2-3 and 5-6, the lock mechanism 54 is illustrated in the macro adjustment mode. A surgeon or operator can press the macro switch 68 in the direction D4 (FIG. 7) to overcome the bias force of the first spring member 70. The macro switch 68 is moveable in the direction D4 to cause the lock threading LT to disengage the shaft threading ST such that the reaming head 46 is translatable along the longitudinal axis A in response to sliding the housing 22 along a length of the drive shaft 38 in an axial direction D6 (FIG. 3). The micro switch 66 is moveable in the direction D2 such that the retention member 72 engages the second recess 66G of the lock body 66A to set the second position of the micro switch 66. The engagement portion 66E engages one of the interfaces 49 along the drive shaft 38 to block or otherwise limit relative rotation between the housing 22 and drive shaft 38.

Referring to FIG. 10, with continuing reference to FIGS. 2-3 and 5-9, the lock mechanism 54 is shown in the locked mode. A surgeon or operator can depress the macro switch 68 such that the first spring member 70 outwardly biases the macro switch 68 in the direction D3. The micro switch 66 can be set such that the engagement portion 66E engages with one of the interfaces 49 to block or otherwise limit relative rotation between the housing 22 and drive shaft 38.

FIGS. 11-12 illustrate an exemplary reaming assembly 120 that can be utilized for various surgical procedures, including in any of the procedures disclosed herein. The reaming assembly 120 can be utilized alone and/or in combination with any of the reaming assemblies disclosed herein, including the reaming assembly 20. The reaming assembly 120 includes a rotatable drive shaft 138. A proximal end portion 142 of the drive shaft 138 can be coupled to tooling T (shown in dashed lines in FIG. 11 for illustrative purposes) to rotate the drive shaft 138 in a rotational direction R1 about the longitudinal axis A.

In the illustrative embodiment of FIG. 12, the drive shaft 138 is cannulated drive shaft including an inner bore 147 dimensioned to extend along the longitudinal axis A. The inner bore 147 can be dimensioned to at least partially receive a guide pin GP (shown in dashed lines for illustrative purposes). The reaming assembly 120 can be translated along the guide pin GP to engage surfaces of the surgical site at a selected location and/or orientation.

The reaming assembly 120 includes a reaming head 146 coupled to the distal end portion 144 of the drive shaft 138. The reaming head 146 includes a reaming portion 148 extending radially outwardly from a nose portion 150. The reaming head 146 includes cutting (or reaming) teeth 152 extending along the reaming portion 148. The nose portion 150 can be free of any cutting teeth and can serve as a guide for alignment of the reaming head 146 relative to a recess or bone hole previously formed in the surgical site. The cutting teeth 152 are rotatable in the rotational direction R1 about the longitudinal axis A to remove bone or other tissue from a surgical site. In embodiments, a diameter and/or length of the nose portion 150 is approximately equal to a diameter and/or length of the nose portion 50 of the reaming assembly 20, and a diameter of the reaming portion 148 is greater than a diameter of the reaming portion 48 of the reaming assembly 20. For the purposes of this disclosure, the term "approximately" means±5 percent of the stated value unless otherwise disclosed. The reaming assembly 120 can be utilized to perform a secondary reaming operation to widen a portion of a bone hole subsequent to performing a primary reaming operation with the reaming assembly 20 at the surgical site, for example.

FIGS. 13-14 illustrate an exemplary reaming assembly 220 that can be utilized for various surgical procedures, including in any of the procedures disclosed herein. The reaming assembly 220 can be utilized alone and/or in combination with any of the reaming assemblies disclosed herein, including the reaming assembly 20. The reaming assembly 220 includes a rotatable drive shaft 238 coupled to a reaming head 246. A proximal end portion 242 of the drive shaft 238 can be coupled to tooling T (shown in dashed lines in FIG. 14 for illustrative purposes) to rotate the drive shaft 238 in a rotational direction R1 about the longitudinal axis A.

The nose portion 250 has a generally cylindrical geometry and extends outwardly from a shaft cavity 251. In embodiments, a diameter and/or length of the nose portion 250 is approximately equal to a diameter and/or length of the nose portion 50 of the reaming assembly 20, and a diameter of the reaming portion 248 is greater than a diameter of the reaming portion 48 of the reaming assembly 20. The reaming assembly 220 can be utilized to perform a secondary reaming operation to widen a portion of a bone hole subsequent to performing a primary reaming operation with the reaming assembly 20 at the surgical site, for example.

The nose portion 250 can be free of any cutting teeth. A retention member 253 such as a pin or fastener abuts a flange 250A of the nose portion 250 to capture the nose portion 250 in the shaft cavity 251 (see FIG. 14). A third spring member 255 is dimensioned to extend between a wall of the shaft cavity 251 and an end of the nose portion 250 to bias or urge the nose portion 250 in a direction D7 (FIG. 14) along the longitudinal axis A. Various spring configurations can be utilized for the spring member 255, including any of the spring configurations disclosed herein.

The reaming assembly 220 includes at least one elongated viewing window 257 along a sidewall of the drive shaft 238. The reaming assembly 220 includes a depth ruler DR (FIG. 13). A proximal end of the nose portion 250 serves as a depth indicator DI (FIG. 14). In another embodiment, a depth indicator DI is provided along a periphery of the nose portion 250. The depth ruler DR and depth indicator DI are moveable relative to each other. The depth indicator DI is axially aligned with a selected value along the depth ruler DR relative to the longitudinal axis A. The depth ruler DR can correspond to a range of reaming depths.

FIGS. 15-17 illustrate an exemplary depth gauge instrument 376 that can be utilized for determining a dimension of a surgical site. Although the instruments and surgical sites disclosed herein primarily refer to a glenoid of a patient, it should be appreciated that the instruments may be utilized for a variety of bony surfaces and other anatomical surfaces of a patient. For example, the depth gauge instruments disclosed herein can be utilized to measure or determine a dimension of a defect, contour or topology along the surgical site.

Referring to FIGS. 15-16, the instrument 376 includes a gauge housing 378 and at least one control member 380 secured to the gauge housing 378. The gauge housing 378 includes a main body 378A extending along a longitudinal axis X between a proximal end portion 378B and a distal end portion 378C. The main body 378A can have a generally cylindrical geometry. The main body 378A includes a passageway 378P extending between the proximal and distal end portions 378B, 378C, as illustrated in FIG. 16.

The gauge housing 378 includes a stop sleeve (or hood) 378D extending radially outwardly from the main body 378A along the distal end portion 378C. The stop sleeve 378D has a generally bell-shaped geometry and defines a terminal end 378E of the gauge housing 378. The terminal end 378E is substantially planar and extends along a reference plane that is substantially perpendicular to the longitudinal axis X. The stop sleeve 378D is dimensioned to contact or abut tissue such as bone along the terminal end 378E.

The gauge housing 378 can be dimensioned with respect to a dimension of the reaming assembly 20. In the illustrative embodiment of FIG. 3, the hood 32 of the reaming assembly 20 is dimensioned to establish a width W1 between the longitudinal axis A and a circumference or perimeter 33 of the hood 32 along the terminal end 34. In the illustrative embodiment of FIG. 15, the stop sleeve 378D of the instrument 376 is dimensioned to establish a width W2 between the longitudinal axis X and a perimeter 378F of the stop sleeve 378D. The width W2 can be approximately equal to the width W1.

The control member 380 is moveable relative to the gauge housing 378 to determine a dimension of a surgical site. In the illustrative embodiment of FIGS. 15-16, the instrument 376 includes a single control member 380. The control member 380 is an elongated actuation shaft including a control body 380A extending along the longitudinal axis X between proximal and distal end portions 380B, 380C. The control member 380 is slidably received and free floating in the passageway 378P. A length of the control member 380 is greater than a length of the gauge housing 378 such that the control member 380 extends outwardly from the proximal and/or distal end portions 378B, 378C of the gauge housing 378 in an installed position.

A terminal end 380T (or nose) of the control member 380 is established along the distal end portion 380C. The terminal end 380T is dimensioned to contact or abut tissue such as bone along a surgical site S adjacent to the terminal end 378E of the gauge housing 378, as illustrated by FIG. 17.

The control member 380 can include an elongated passageway 380P dimensioned to at least partially receive a guide pin GP (shown in dashed lines in FIG. 16 for illustrative purposes). In other embodiments, the passageway 380P is omitted such that the control member 380 is substantially solid.

Referring to FIGS. 15 and 17, the instrument 376 includes a depth ruler MDR and a depth indicator MDI moveable relative to the depth ruler MDR to measure a thickness or depth of a defect, contour or topology along the surgical site S. The gauge housing 378 includes an opening 378G formed in a sidewall of the main body 378A. The opening 378G can be a window or elongated slot, for example. The depth ruler MDR is established along the opening 378G. The depth indicator MDI is axially aligned with the opening 378G and a selected value along the depth ruler MDR relative to the longitudinal axis X. The depth ruler MDR is dimensioned with respect to a range of depths or thicknesses for measuring a defect, contour or topology along the surgical site S. The depth ruler MDR can include circumferential markings on a periphery of the gauge housing 378, for example. The depth indicator MDI is moveable relative to the depth ruler MDR in response to relative movement between the control member 380 and gauge housing 378.

In embodiments, alignment of the depth indicator MDI and a selected value along the depth ruler MDR corresponds to a measured depth MRD. The measured depth MRD can be defined as a distance between a distal-most portion of the terminal end 378E of the gauge housing 378 and the terminal end 380T of the control member 380.

The depth ruler MDR can be dimensioned with respect to the range of reaming depths RD of the reaming head 46 of the reaming assembly 20 (see FIG. 3). In embodiments, a range of values along the depth ruler MDR of the instrument 376 corresponds to a range of values along the depth ruler DR of the reaming assembly 20. A surgeon can translate or otherwise move the control member 380 along the longitudinal axis X to determine the measured depth MRD. The surgeon can utilize the measured depth MRD determined by a position of the depth indicator MDI relative to the depth ruler MDR to set a position of the depth indicator DI relative to the depth ruler DR and thereby set the reaming depth RD of the reaming assembly 20.

Figure 18:
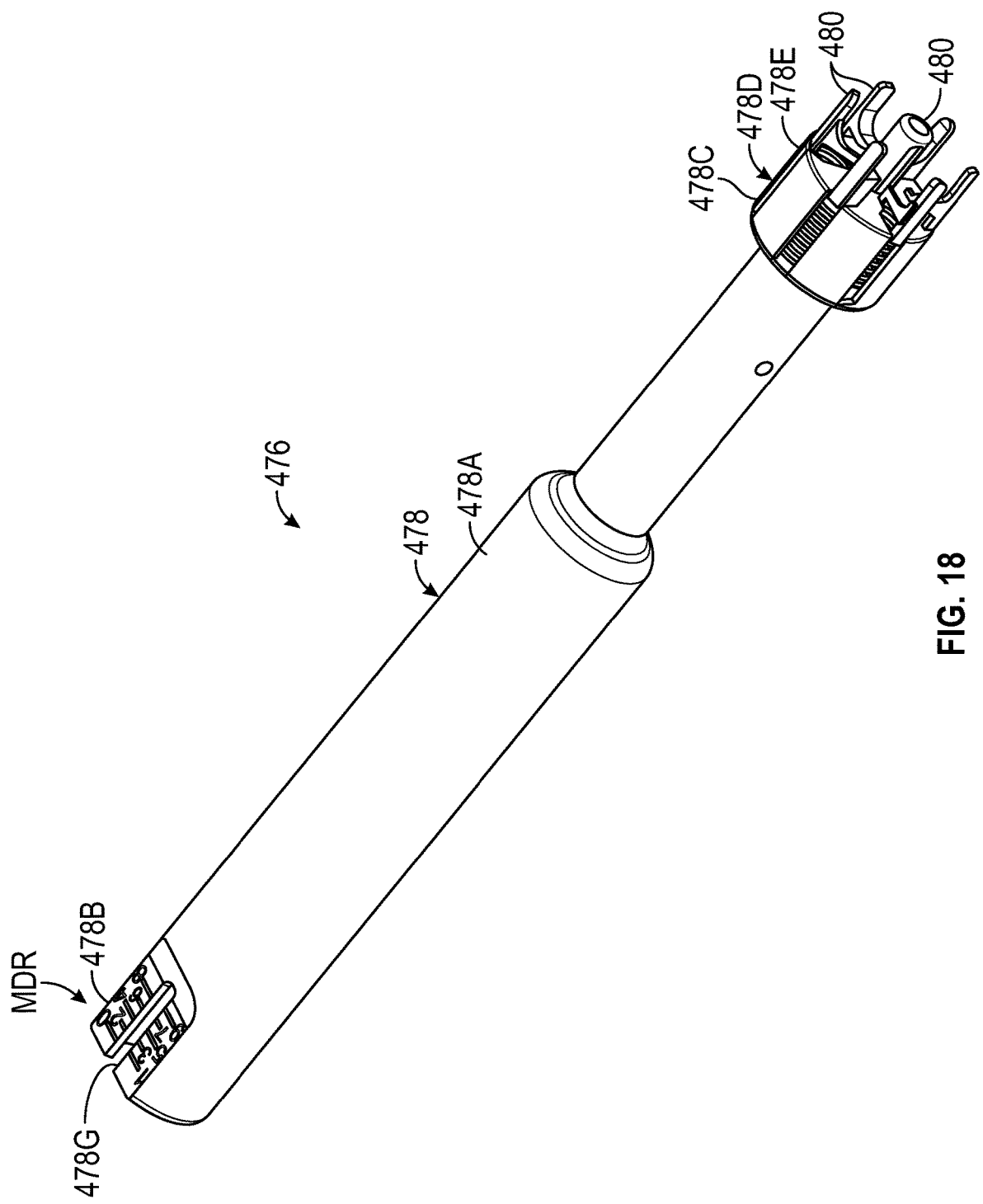
FIG. 18 illustrates a perspective view of an exemplary depth gauge instrument for evaluating a surgical site according to another embodiment.
Figure 19:
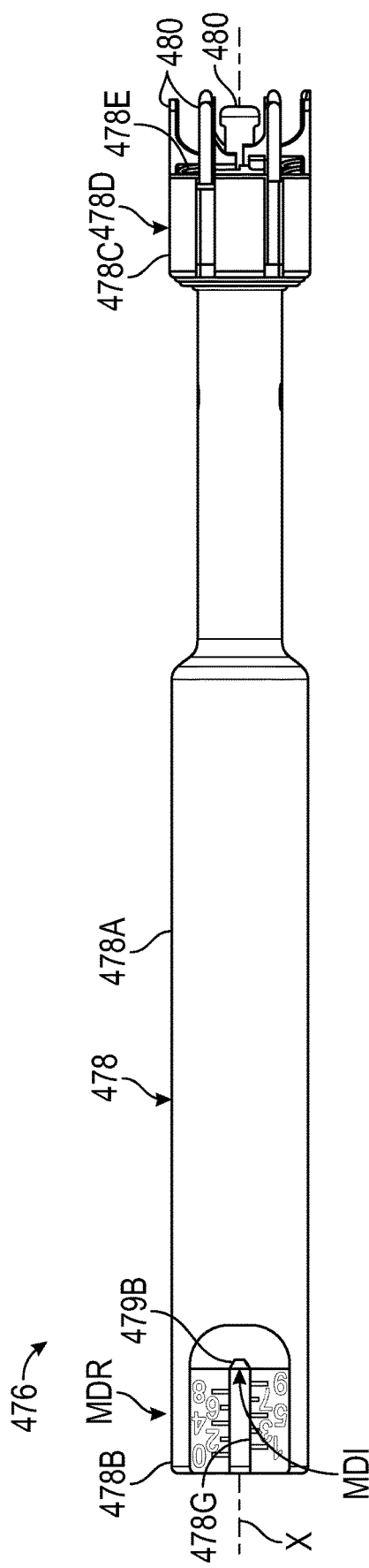
FIG. 19 illustrates a side view of the depth gauge instrument of FIG. 18.

FIGS. 18-25 illustrate another exemplary depth gauge instrument 476 that can be utilized for determining a dimension of a surgical site. Referring to FIGS. 18-19, the instrument 476 includes one or more control members 480 secured to a gauge housing 478. The gauge housing 478 includes a main body 478A extending along a longitudinal axis X (FIG. 19) between proximal and distal end portions 478B, 478C. The main body 378A can include one or more portions each having a generally cylindrical geometry.

The gauge housing 478 includes an opening 478G formed in a sidewall of the main body 478A. In the illustrative embodiment of FIGS. 18-19, the opening 478G is an elongated slot established along the proximal end portion 478B. The instrument 476 includes a depth ruler MDR and a depth indicator MDI. The depth ruler MDR is established along the opening 478G. The depth indicator MDI is axially aligned with a selected value along the depth ruler MDR relative to the longitudinal axis X.

Figure 20:
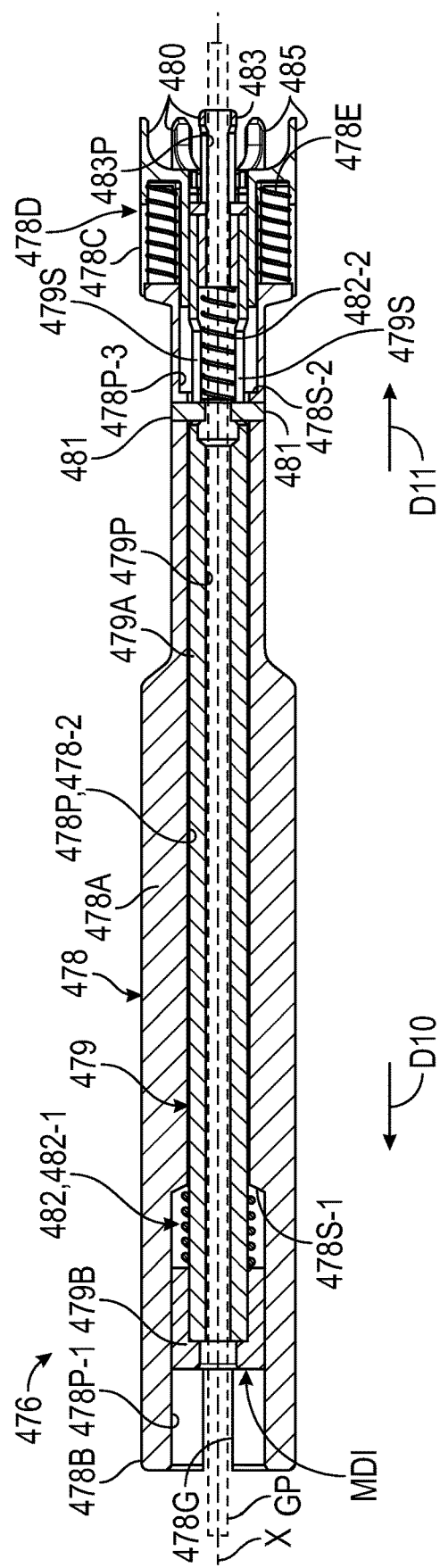
FIG. 20 illustrates a sectional view of the depth gauge instrument of FIG. 19.
Figure 21:
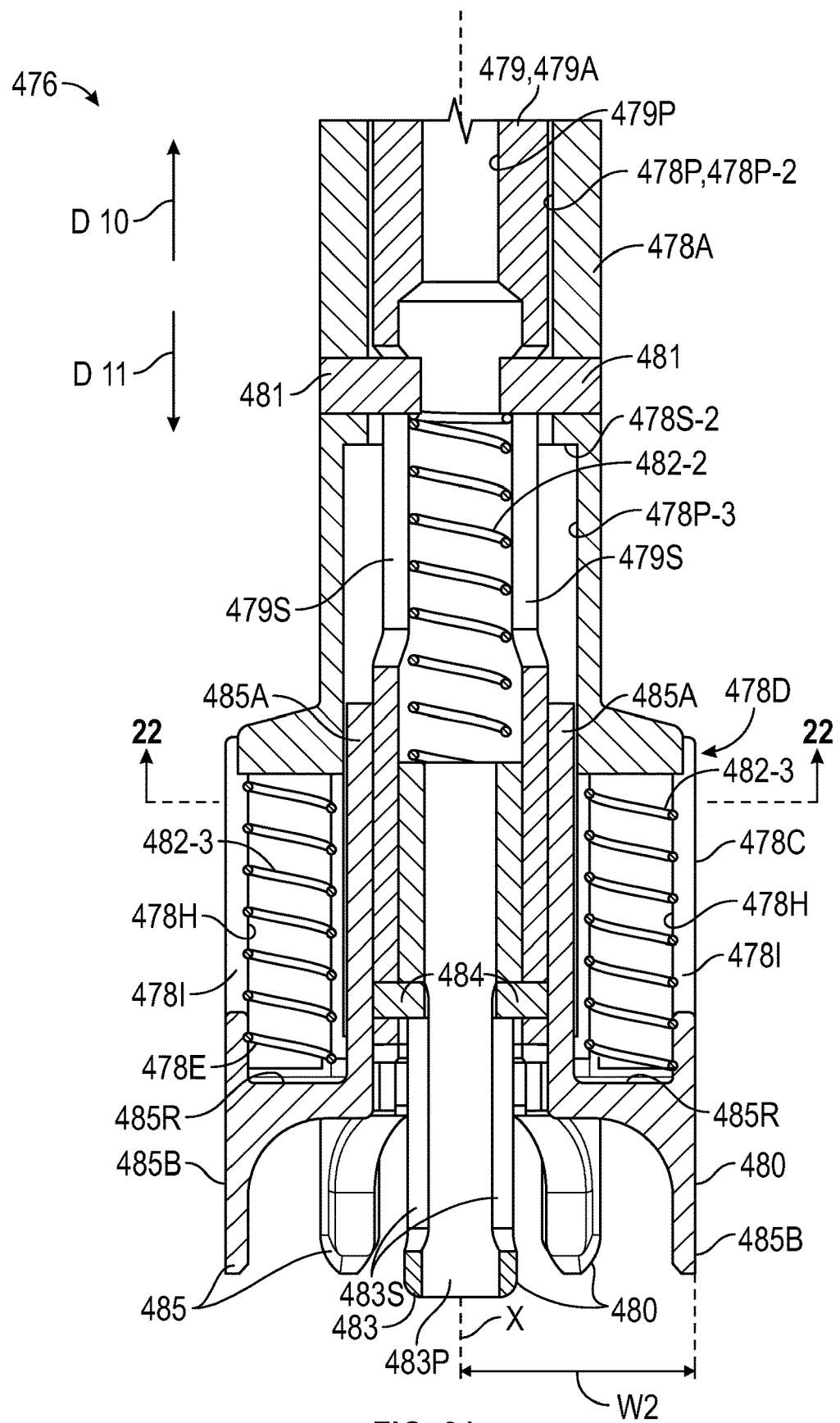
FIG. 21 illustrates selected portions of the depth gauge instrument of FIG. 20.
Figure 24:
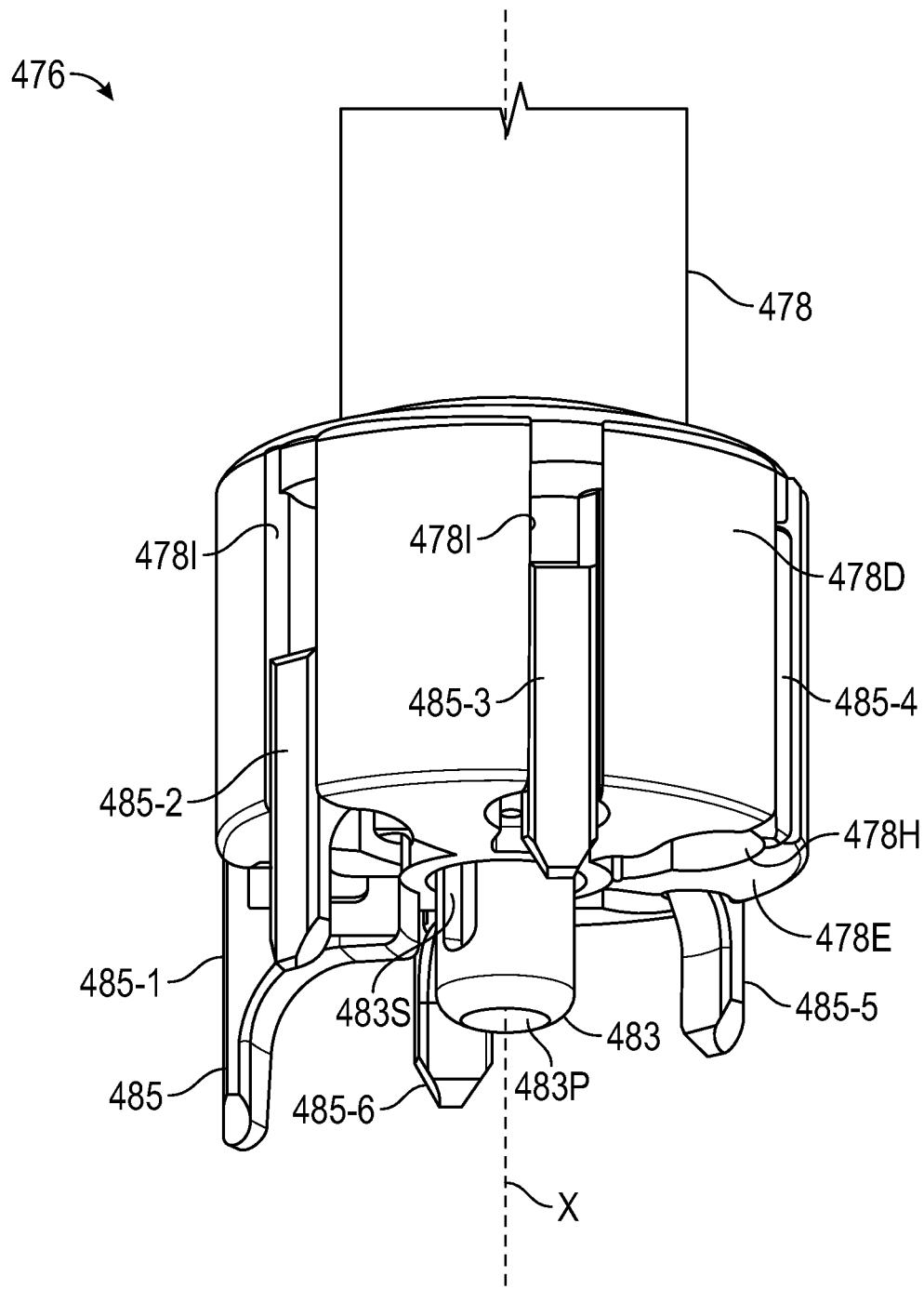
FIG. 24 illustrates a perspective view of selected portions of the depth gauge instrument of FIG. 18 including control members at various positions.

Referring to FIGS. 20-21, with continuing reference to FIGS. 18-19, the gauge housing 478 includes a stop sleeve (or hood) 478D secured to the main body 478A to establish the distal end portion 478C. In the illustrative embodiment of FIGS. 20-21, the stop sleeve 478D and main body 478A are separate and distinct components. In other embodiments, the stop sleeve 478D and main body 478A are a single component. The stop sleeve 478D has a generally cylindrical geometry and defines a terminal end 478E of the gauge housing 478. The terminal end 478E can be substantially planar, or can be generally convex as illustrated by FIG. 24. The stop sleeve 478D is dimensioned to contact or abut tissue such as bone along the terminal end 478E.

The main body 478A includes a passageway 478P extending between the proximal and distal end portions 478B, 478C. The passageway 478P includes proximal, intermediate and distal sections 478P-1, 478P-2 and 478P-3. The intermediate section 478P-2 interconnects the proximal and distal sections 478P-1, 478P-3. The proximal and distal sections 478P-1, 478P-3 extend radially outward of the intermediate section 478P-2 to establish respective shoulders 478S-1, 478S-2.

The instrument 476 includes an actuation shaft 479 concentric with the gauge housing 478. The actuation shaft 479 is slidably received in the passageway 478P such that the shaft 479 extends along the longitudinal axis X. The actuation shaft 479 includes a first portion 479A coupled to a second portion 479B (FIG. 20). In the illustrated embodiment of FIGS. 20-21, the actuation shaft 479 is a cannulated shaft including a passageway 479P dimensioned to at least partially receive a guide pin (shown in dashed lines in FIG. 20 for illustrative purposes).

A face of the second portion 479B of the actuation shaft 479 can serve as the depth indicator MDI, as illustrated by FIGS. 19-20, for example. In other embodiments, the depth indicator MDI is a marking along the actuation shaft 479. The depth indicator MDI is moveable relative to the depth ruler MDR in response to relative movement between the actuation shaft 479 and gauge housing 478 to measure a thickness or depth of a defect, contour or topology along a surgical site.

The actuation shaft 479 includes a pair of opposed slots 479S extending through a sidewall of the first portion 479A of the actuation shaft 479. A pair of retention pins 481 are secured to the gauge housing 478. Each retention pin 481 is received in a respective slot 479S to secure the actuation shaft 479 to the gauge housing 478. Each retention pin 481 is dimensioned to selectively abut against opposed ends of the slot 479S to limit axial movement of the actuation shaft 479 relative to the longitudinal axis X.

The instrument 476 includes one or more spring members 482 received in the gauge housing 478 to selectively actuate a respective control member 480. Various spring configurations can be utilized for the spring members 482, including any of the spring configurations disclosed herein. In the illustrative embodiment of FIG. 20, the spring members 482 include a first spring member 482-1 received in the proximal section 478P-1 of the passageway 478P. The first spring member 482-1 can be a coil spring extending about an outer diameter of the first portion 479A of the actuation shaft 479, for example, and is captured between the second portion 479B of the actuation shaft 479 and the shoulder 478S-1. The first spring member 482-1 is dimensioned to bias the actuation shaft 479 in direction D10, which can be generally parallel to the longitudinal axis X.

In the illustrative embodiment of FIGS. 20-21, the instrument 476 includes a plurality of control members 480 secured to the stop sleeve 478D. Each of the control members 480 is selectively moveable between respective first and second positions relative to the longitudinal axis X and the terminal end 478E of the gauge housing 478 to selectively contact or abut tissue such as bone along a surgical site. The control members 480 include a central control leg 483 extending along the longitudinal axis X and a set of peripheral control legs 485 circumferentially distributed about the central control leg 483. The instrument 476 includes a quantity of six peripheral control legs 485 (indicated at 485-1 to 485-6 in FIGS. 24-25). It should be appreciated that fewer or more than six peripheral control legs 485 may be utilized. For example, the instrument 476 can include the central control leg 483 and only one peripheral control leg 485. In embodiments, the central control leg 483 is omitted. In the illustrative embodiment of FIG. 21, each peripheral control leg 485 is arranged to establish a width W2 between a terminal end of the peripheral control leg 485 and the longitudinal axis X. The width W2 can be approximately equal to the width W1 of the reaming assembly 20 (see FIG. 3).

Figure 23A:
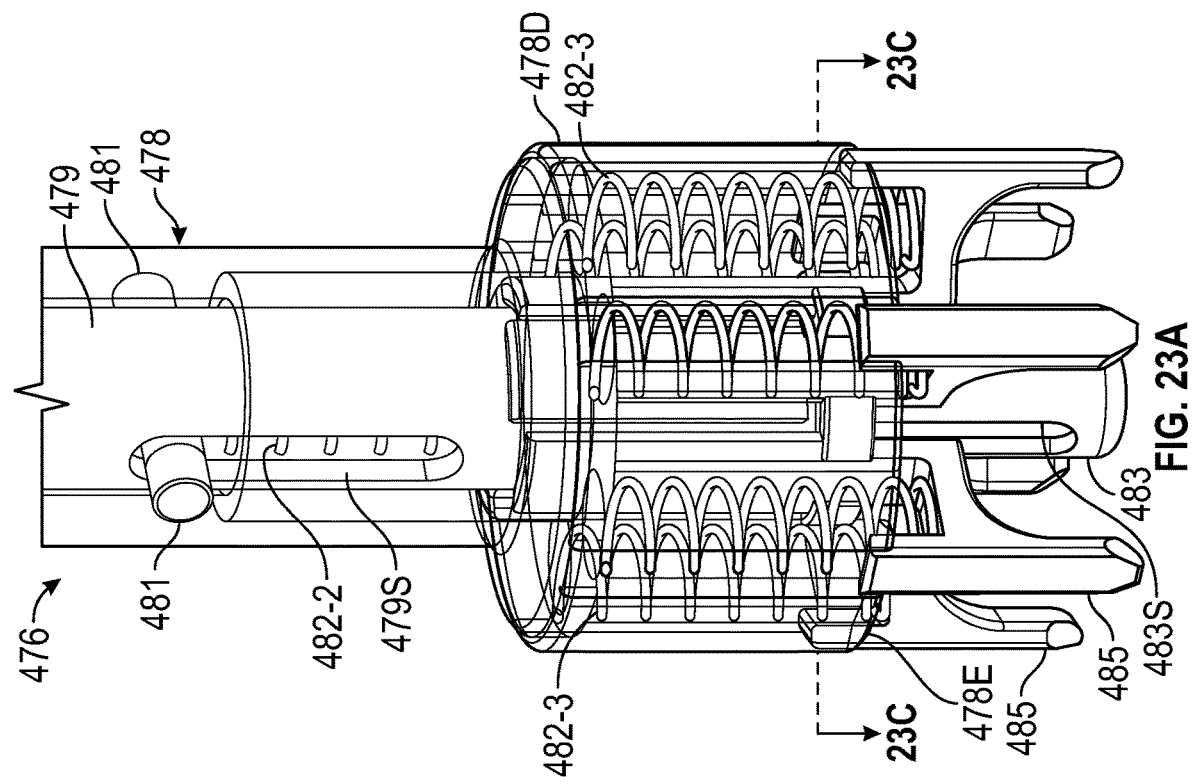
FIG. 23A illustrates a perspective view of selected portions of the depth gauge instrument of FIG. 18 with a gauge housing shown in phantom and control members at various positions.

The control members 480 can have various profiles. In the illustrative embodiment of FIG. 21, the central control leg 483 has a generally tubular geometry and is concentric with the actuation shaft 479. In the illustrative embodiment of FIGS. 21 and 23B, each peripheral control leg 485 includes a first leg portion 485A and a second leg portion 485B. The first leg portion 485A has a substantially L-shaped geometry and extends outwardly from an intermediate position along the second leg portion 485B such that a cross section of the peripheral control leg 485 has a generally S-shaped geometry. A recess 485R is established between the first and second leg portions 485A, 485B. A portion of the first leg portion 485A is slidably received in a respective groove 479G along an outer diameter of the actuation shaft 479, as illustrated by FIGS. 23B-23C (see also FIG. 23A).

Referring to FIGS. 21 and 23C, the central control leg 483 is received in, and extends outwardly from, the passageway 479P of the actuation shaft 479. The central control leg 483 can be cannulated and can include a passageway 483P dimensioned to receive a guide pin GP (see FIG. 20). A pair of opposed slots 483S extend along and through a sidewall of the central control leg 483 (see also FIG. 24). A pair of retention pins 484 are secured to the actuation shaft 479. Each retention pin 484 is received in a respective slot 483S to secure the central control leg 483 to the gauge housing 478 via the actuation shaft 479. Each retention pin 484 is dimensioned to selectively abut against opposed ends of the slot 483S to limit relative axial movement between the central control leg 483 and actuation shaft 479 with respect to the longitudinal axis X.

Figure 22:
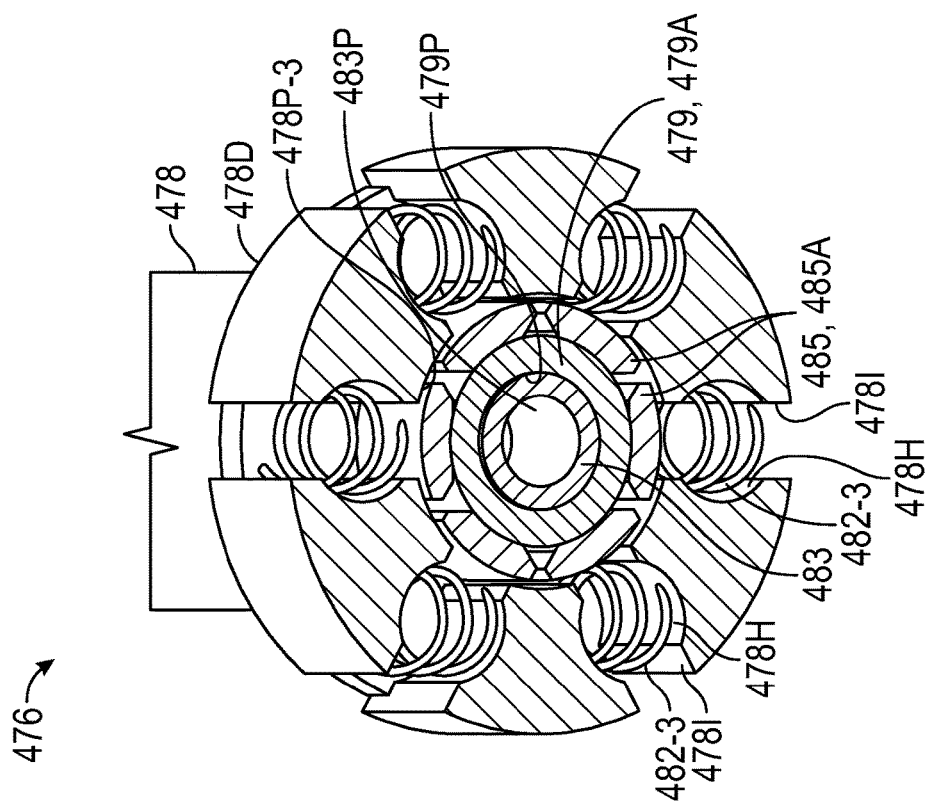
FIG. 22 illustrates a sectional view of the depth gauge instrument taken along line 22-22 of FIG. 21.

The stop sleeve 478D includes a plurality of spring cavities 478H extending inwardly from the terminal end 478E of the gauge housing 478 (see also FIG. 22). Each spring cavity 478H extends between the distal section 478P-3 of the passageway 478P and a respective slot 478I defined along an outer wall of the stop sleeve 478D. Each spring cavity 478H can be dimensioned to selectively receive at least a portion of a respective peripheral control leg 485.

The control legs 483, 485 are longitudinally outwardly biased relative to the distal end portion 478C of the gauge housing 478 to selectively contact an adjacent surface of a surgical site. The spring members 482 include a central spring member 482-2 (FIG. 21) and a set of peripheral spring members 482-3. The first spring member 482-1 (FIG. 20) can be selected to have a relatively lesser biasing force (e.g., weak) than a biasing force (e.g., strong) of the central spring member 482-2 and/or peripheral spring members 482-3.

The central spring member 482-2 is captured in the passageway 479P between the retention pins 481 and a proximal end of the central control leg 483, as illustrated by FIG. 21. The central spring member 482-2 is dimensioned to bias the central control leg 483 in direction D11, which is generally opposed to the direction D10 (FIG. 21). The central spring member 482-2 is dimensioned to bias the actuation shaft 479 in the direction D11 in response to abutment of one or more of the retention pins 484 and a proximal end of the respective slot 485.

Each peripheral spring member 482-3 is received in a respective spring cavity 478H and in the recess 485R of a respective one of the peripheral control legs 485 such that the spring member 482-3 is captured between a wall of the stop sleeve 478D and a wall of the respective control leg 485.

Figure 25:
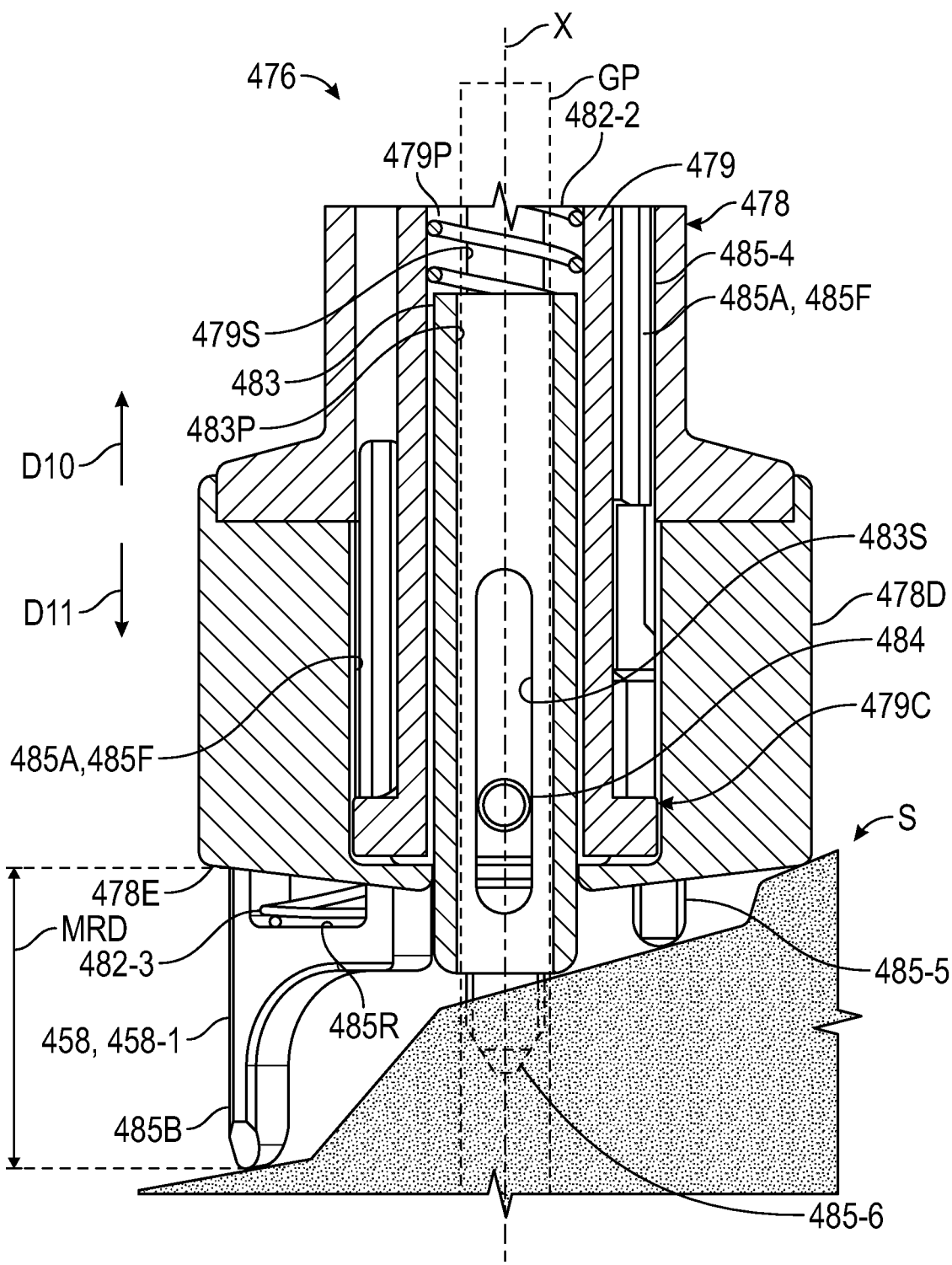
FIG. 25 illustrates a sectional view of the depth gauge instrument of FIG. 24 including the control members situated relative to a surgical site.

FIGS. 23A-23C illustrate the control legs 483, 485 at various positions relative to the gauge housing 478. FIGS. 24-25 illustrate the control legs 483, 485 at various positions relative to the terminal end 478E of the gauge housing 478, which may differ from the positions of the control legs 483, 485 of FIGS. 23A-23C. FIG. 25 illustrates the instrument 476 positioned relative to a surgical site S along a guide pin GP (shown in dashed lines for illustrative purposes). A surface of the surgical site S may be generally uneven and/or sloped, for example.

Referring to FIGS. 24-25, with continuing reference to FIG. 19, the instrument 476 provides a reading along the depth ruler MDR based on a position of a longitudinally outermost one of the control legs 483, 485 relative to the longitudinal axis X. The actuation shaft 479 is configured to set a position of the depth indicator MDI relative to the depth ruler MDR based on a longitudinally outermost position of the control legs 483, 485 relative to the longitudinal axis X and/or terminal end 478E of the gauge housing 478. The control legs 483, 485 are dimensioned such that the actuation shaft 479 causes relative movement between the depth indicator MDI and depth ruler MDR in response to movement of a longitudinally outermost one of the control legs 483, 485.

Referring to FIGS. 23B and 25, with continuing reference to FIG. 24, each of the peripheral control legs 485 includes at least one or a pair of flanges 485F extending outwardly from opposed sides of the first leg portion 485A. The actuation shaft 479 includes a control member 479C. In the illustrative embodiment of FIGS. 23B and 25, the control member 479C is a segmented ledge or flange dimensioned to selectively abut one or more of the peripheral control legs 485. The spring members 482-3 outwardly bias the control legs 485 such that the control legs 485 selectively engage the control member 479C (see, e.g., control leg 480-2 of FIG. 25) to urge the actuation shaft 479 in direction D11. It should be appreciated that the flange(s) 485F of more than one of the peripheral control legs 485 can simultaneously contact the control member 479C while the flange(s) 485F of other peripheral control leg(s) 485 may not, as illustrated by the position of the control legs 485 of FIGS. 23A-23B.

Referring to FIG. 25, with continuing reference to FIGS. 19, 21 and 23B, contact between the control member 479C and flanges 485F of the longitudinally outermost control leg 485 or between the retention pin(s) 484 and proximal face of the respective slot 483S of the central control leg 483 urges the actuation shaft 479 in the direction D11 and sets a position of the depth indicator MDI. Contact between a distal end of the control leg 483/485 and an adjacent surface of the surgical site S causes the respective control leg 483/485 to move in direction D10 relative to the longitudinal axis X. The control legs 483, 485 are dimensioned such that a longitudinally outermost one of the control legs 483, 485 establishes contact with the control member 479C or retention pin(s) 484 to set a position of the actuation shaft 479. In the illustrative embodiment of FIG. 25, central control leg 483 and peripheral control legs 485-5, 485-6 are proximal to the peripheral control leg 485-1 such that the peripheral control leg 485-1 sets the position of the depth indicator MDI. However, it should be appreciated that any one of the control legs 483, 485 may be selectively actuated to set a position of the depth indicator MDI.

Alignment of the depth indicator MDI and a selected value along the depth ruler MDR corresponds to a measured depth MRD. The measured depth MRD can be defined as a distance between the terminal end 478E of the gauge housing 478 and a longitudinally outermost position of the control legs 483, 485 relative to the longitudinal axis X (e.g., control leg 485-1 of FIG. 25).

In operation, a surgeon situates the instrument 476 relative to the surgical site S, which can include placing the instrument 476 over the guide pin GP and translating the instrument 476 along the guide pin GP until the terminal end 478E abuts against or contacts a surface of the surgical site S, with each or at least some of the control legs 483, 485 contacting the surface of the surgical site S. A longitudinally outermost one of the control legs 483, 485 (e.g., control leg 485-1) pulls the actuation shaft 479 in the direction D11 to set a position of the depth indicator MDI (FIG. 19). The position of the depth indicator MDI corresponds to a geometry of the instrument 476 and one or more contact points between the terminal end 478E and/or control legs 483, 485 and the adjacent surface of the surgical site S.

Figure 26:
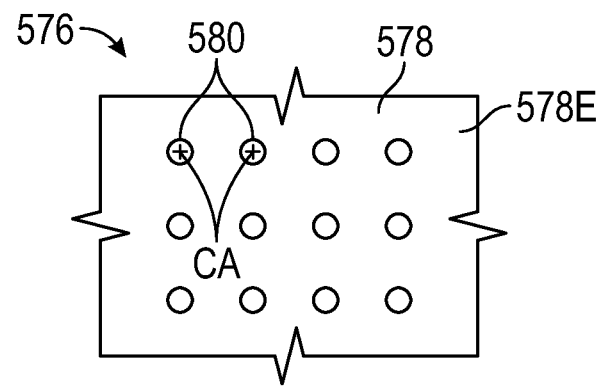
FIG. 26 illustrates an end view of an exemplary depth gauge instrument for evaluating a surgical site according to yet another embodiment.
Figure 27:
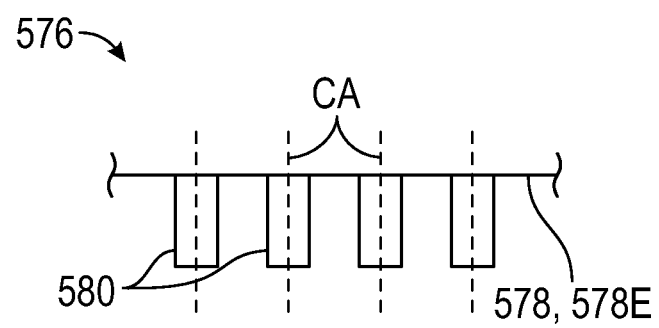
FIG. 27 illustrates a side view of the depth gauge instrument of FIG. 26.

FIGS. 26-27 illustrate yet another exemplary depth gauge instrument 576 that can be utilized for determining a dimension of a surgical site. The instrument 576 includes a plurality of control members 580 secured to a gauge housing 578. The control members 580 are an array of elongated pins arranged in one or more rows and columns to establish a grid, as illustrated by FIG. 26. Each control member 580 is movable along a respective longitudinal axis CA relative to a terminal end 578E of the gauge housing 578.

Figure 28:
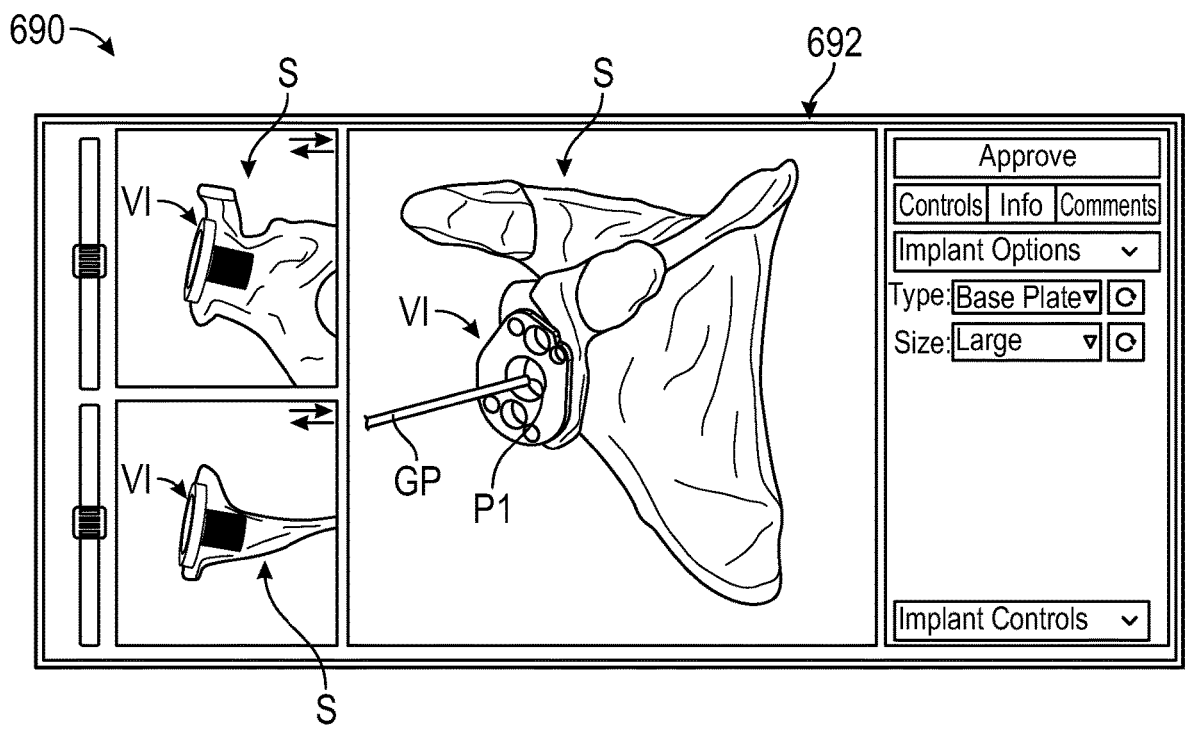
FIGS. 28-31 illustrate an exemplary system for evaluating a surgical site.
Figure 29:
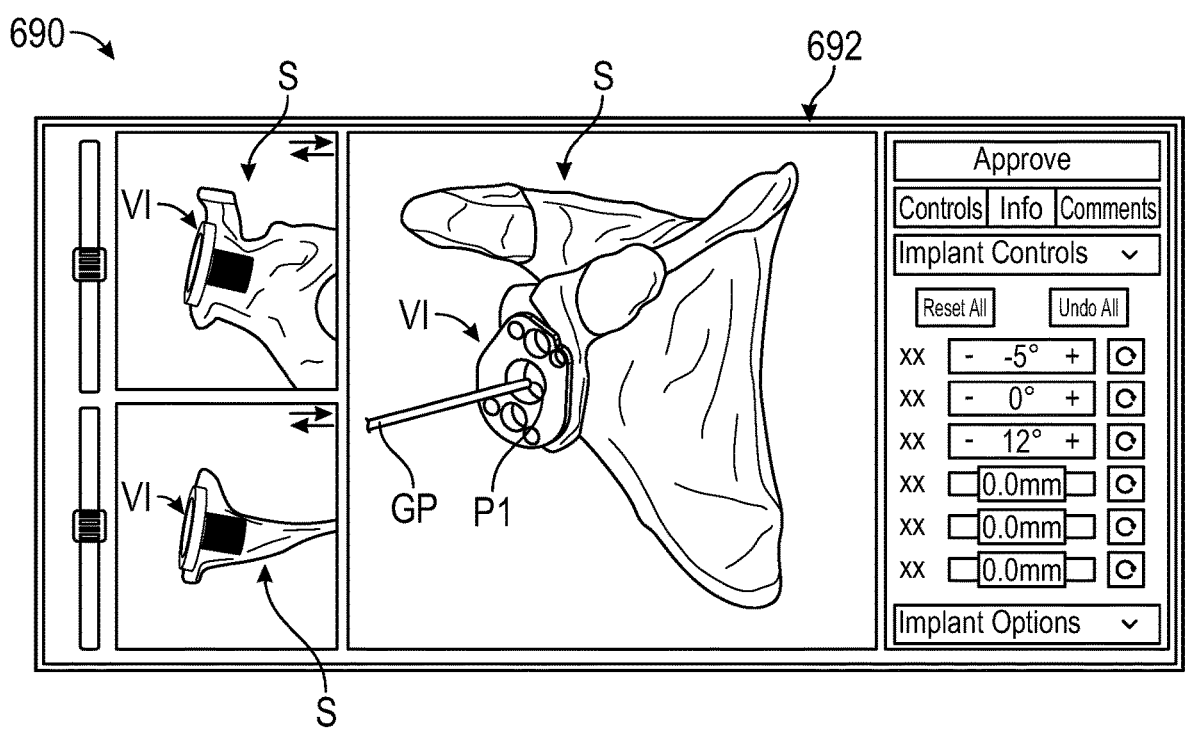
Figure 30:
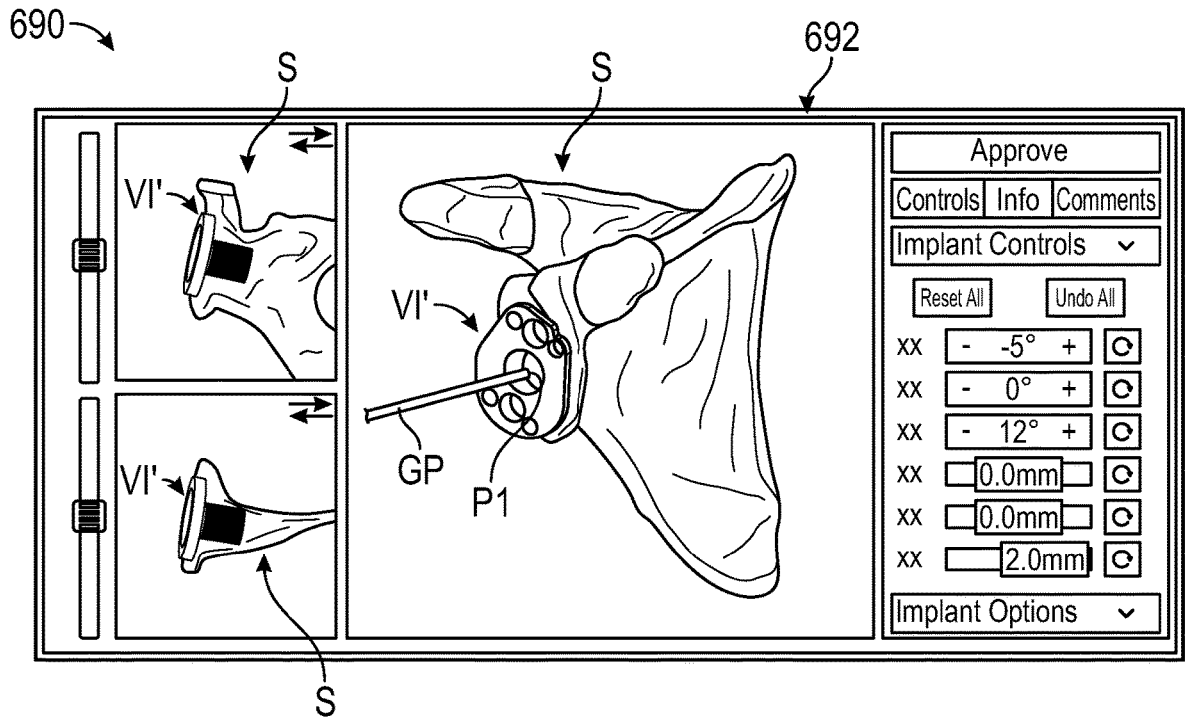

FIGS. 28-30 illustrate an exemplary system 690 for determining a dimension or otherwise evaluating a surgical site. The system 690 can be implemented as one or more software instructions and can incorporate features of the Virtual Implant Positioning™ (VIP) system provided by Arthrex®, Inc., for example. One would understand how to program the system 690 with logic to implement the techniques disclosed herein. FIGS. 28-30 illustrate various states of a model in a graphical user interface 692 of the system 690.

Referring to FIG. 28, the surgeon imports a CT scan, MRI or other preoperative image of a surgical site S such a shoulder of the patient into the system 690. The system 690 is operable to display one or more views of the surgical site S in the graphical user interface 692. The surgeon can interact with menu items of the interface 692 to specify various implant options including implant type and/or size. The various implant options can be preset or imported in the system 690 as one or more data tables, for example. The implant can be a bone plate, for example. In the illustrative embodiment of FIG. 28, the surgeon selects "Arthrex Baseplate" from the "Type" menu item and "Large" from the "Size" menu item. The system 690 is operable to display in the interface 692 a model of the selected implant VI and/or a model of a guide pin GP at a selected position P1 of a model of the surgical site S, as illustrated by the various views of FIG. 28. The selected position P1 can be a default position (e.g., center of the glenoid face) or can correspond to a position of the guide pin GP and/or implant VI manually manipulated by the surgeon through interaction with the interface 692, for example.

Referring to FIG. 29, the surgeon can interact with one or more menu items of the interface 692 to adjust or set an orientation and/or position of the selected implant VI and/or guide pin GP. For example, the surgeon can move the implant VI relative to the Superior/Inferior (S/I) plane and/or Anterior/Posterior (AP) plane by interacting with the "S/I" and/or "A/P" menu bars, respectively.

The surgeon can interact with one or more menu items of the interface 692 to adjust or set a depth of the implant VI such that the implant VI is inset in a surface of the surgical site S, such as by moving the "L/M" menu bar. For example, a negative value may correspond to increasing an inset of the implant VI, and a positive value may correspond to decreasing an inset of the implant VI as illustrated by implant VI' of FIG. 30. The surgeon can interact with one or more menu items of the interface 692 to approve the settings, such as by selection of an "Approve" button.

Figure 31:
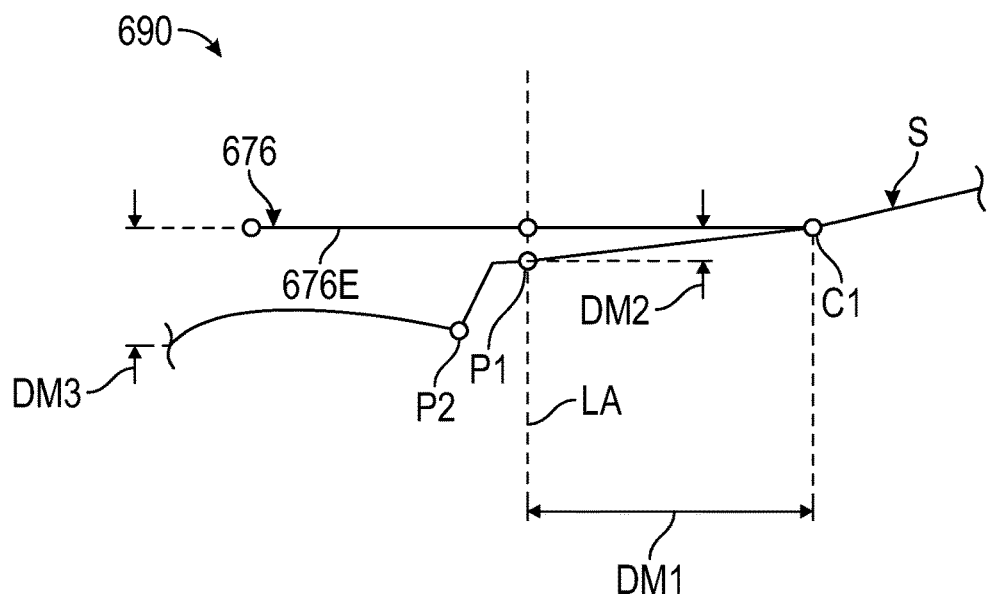

Referring to FIG. 31, with continuing reference to FIGS. 28-30, the system 690 is operable to determine a reaming depth of one or more reaming assemblies based on the approved settings. The system 690 is operable to select a reaming assembly 676 associated with the selected implant VI, or the surgeon can manually select a reaming assembly from a list of available options through interaction with the interface 692. The various reaming assembly options can be preset or imported in the system 690 as one or more data tables, for example. Information relating to the various reaming assembly options can include one or more dimensions of the reaming assemblies disclosed herein, such as maximum and minimum reaming depths and/or the width W1 of the reaming assembly 20 (FIG. 3).

The system 690 determines a contact point C1 between a terminal end 676E of a selected reaming assembly 676 and a surface of the surgical site S based on a geometry of the selected reaming assembly 676 and a geometry or profile of the surgical site S corresponding to one or more preoperative images of the surgical site S. The system 690 is operable to calculate or otherwise determine a distance DM1 between the contact point C1 and a longitudinal axis LA extending through the selected position P1. The longitudinal axis LA can correspond to a position and orientation of the guide pin GP. The system 690 is operable to calculate or otherwise determine a distance DM2 between the selected position P1 and the terminal end 676E of the selected reaming assembly 676 along the longitudinal axis LA. The system 690 is operable to calculate or otherwise determine a distance DM3 between the terminal end 676E of the selected reaming assembly 676 and a position P2 corresponding to a maximum depth along the surgical site S adjacent the terminal end 676E.

The system 690 is operable to calculate or otherwise determine a reaming depth based on the selected depth of the implant VI and distances DM1, DM2 and/or DM3 relating to a geometry of the selected reaming assembly 676 and surgical site S. The system 690 is operable to output or export a reaming depth setting for the selected reaming assembly 676 corresponding to a geometry of the selected implant VI, which can occur in response to selection of the "Approve" button, for example. The selected reaming assembly 676 may correspond to the reaming assembly 20, and the surgeon can then adjust or set the reaming depth RD of the reaming assembly 20 by setting a position of the depth indicator DI relative to the depth ruler DR, for example.

The reaming assemblies, depth gauge instruments and systems disclosed herein, including any of the reaming assemblies 20, 120, 220, depth gauge instruments 376, 476, 576 and system 690, can be provided as a kit for preparation of a surgical site.

Figure 32:
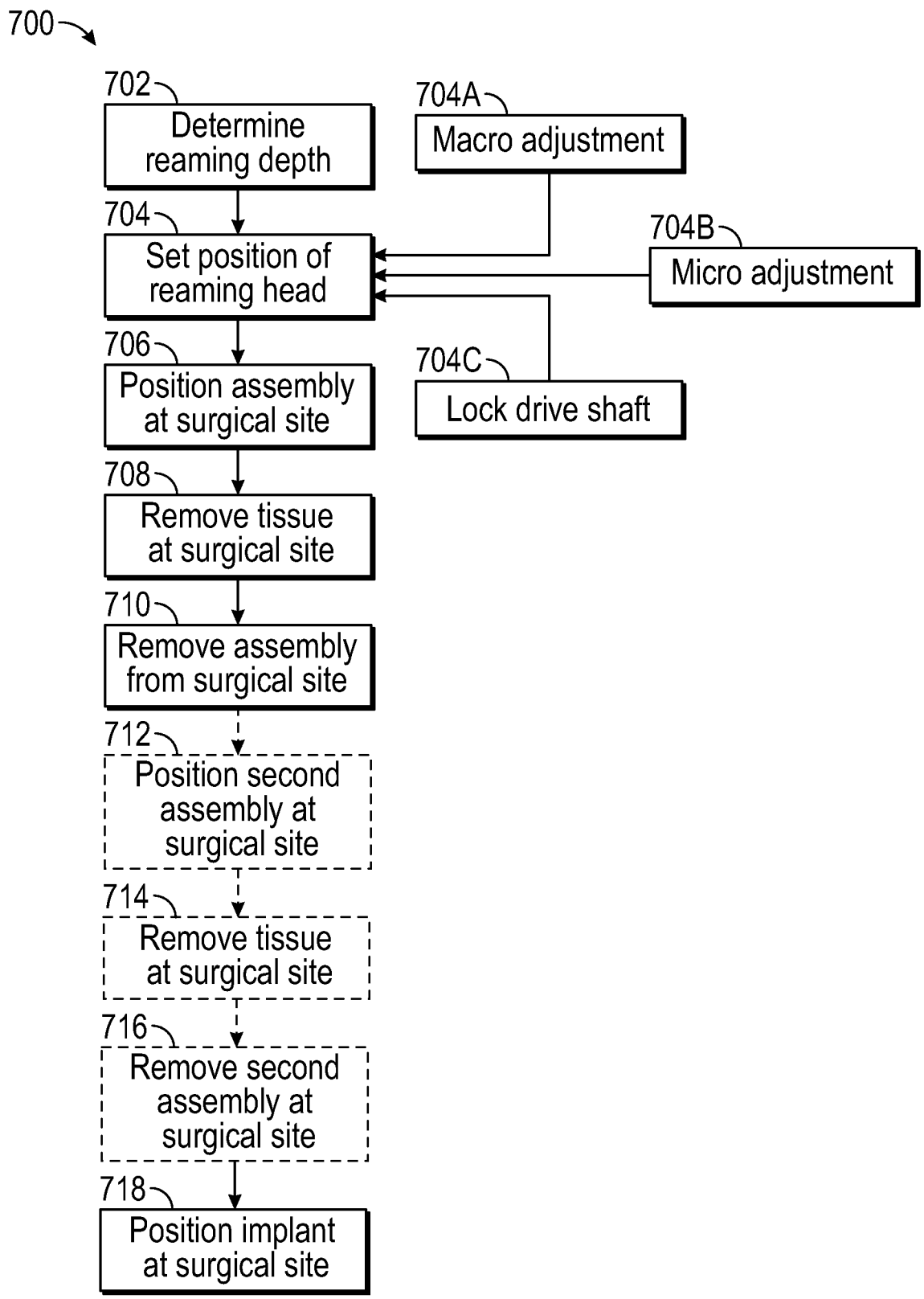
FIG. 32 illustrates an exemplary method for preparing a surgical site.

An exemplary method of use will now be described. Referring to FIG. 32, an exemplary method in a flowchart 700 for preparing a surgical site is shown. Reference is made to the reaming assembly 20 of FIGS. 5-10 and 33-35 and the reaming assemblies 120, 220 of FIGS. 11-14 for illustrative purposes. In should be appreciated that one or more of the steps of method 700 may be performed with the reaming assemblies 20, 120 and/or 220. Reaming assemblies 20, 120 and 220 can be utilized alone or in combination as a kit or reaming system. The method 700 can be utilized to forming a recess or cut at a surgical site, such as a bone hole in an articulating surface of a glenoid. Bone may be removed from a defect in the articulating surface. Fewer or additional steps than are recited below could be performed within the scope of this disclosure, and the recited order of steps is not intended to limit this disclosure.

At step 702, a reaming depth RD is determined. Various techniques can be utilized to determine or select the reaming depth RD. For example, a defect in the glenoid can be characterized by the Walch Classification. The surgeon can measure bone loss utilizing imaging of the surgical site, such a radiogram or computed tomography technique, or can approximate a profile of the defect utilizing one or more sizers and/or measuring devices placed against the bone surface. The reaming depth RD parameter can be selected to approximate the profile of the defect. In embodiments, step 702 includes utilizing any of the reaming depth instruments 376, 476 and/or system 690 disclosed herein to measure or determine a dimension of a defect, contour or topology of a surface along a surgical site, and utilizing the measured information to select the reaming depth RD.

Figure 33:
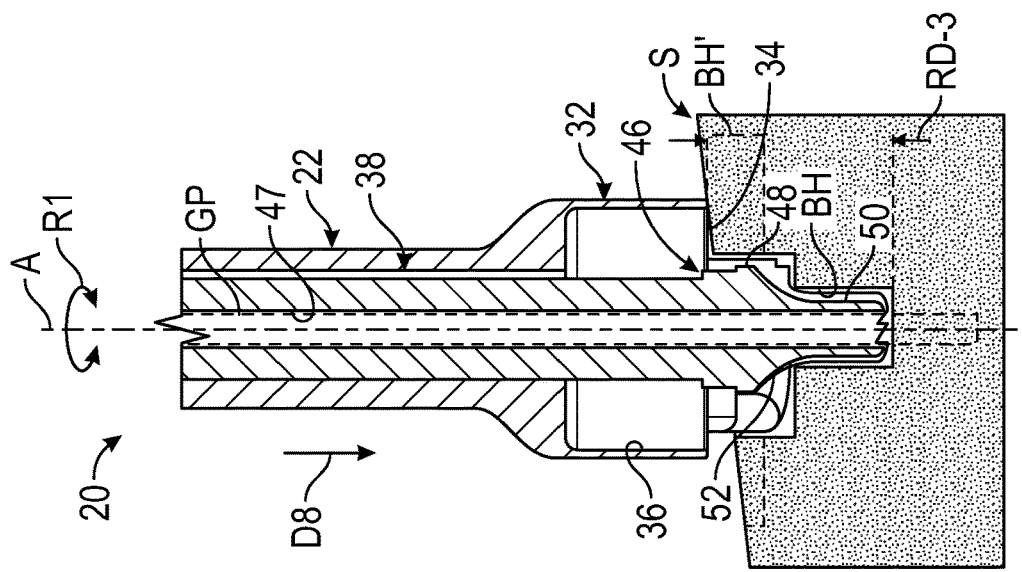
FIGS. 33-35 schematically illustrate selected portions of the reaming assembly of FIG. 1 set at different reaming depths and positioned at a surgical site.
Figure 34:
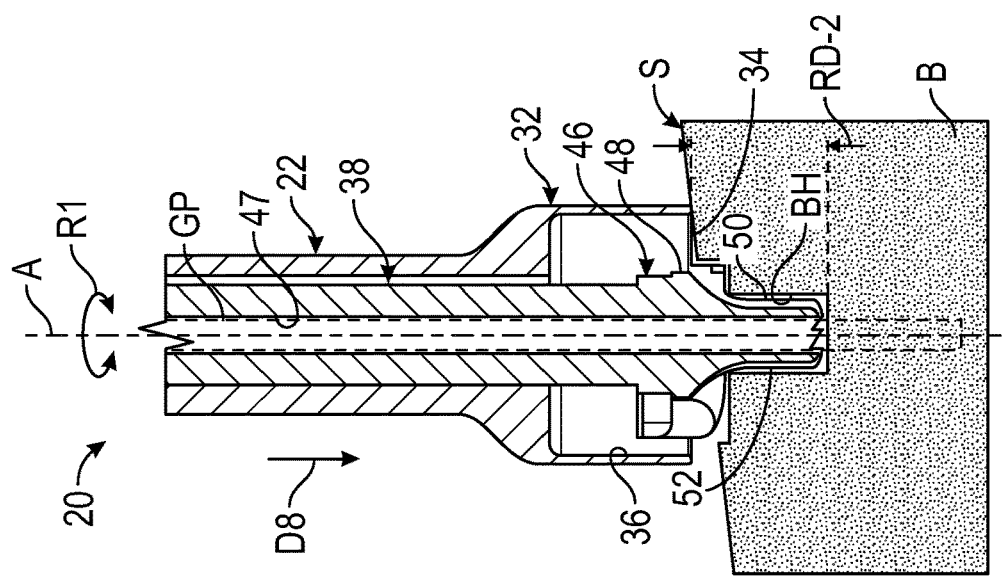
Figure 35:
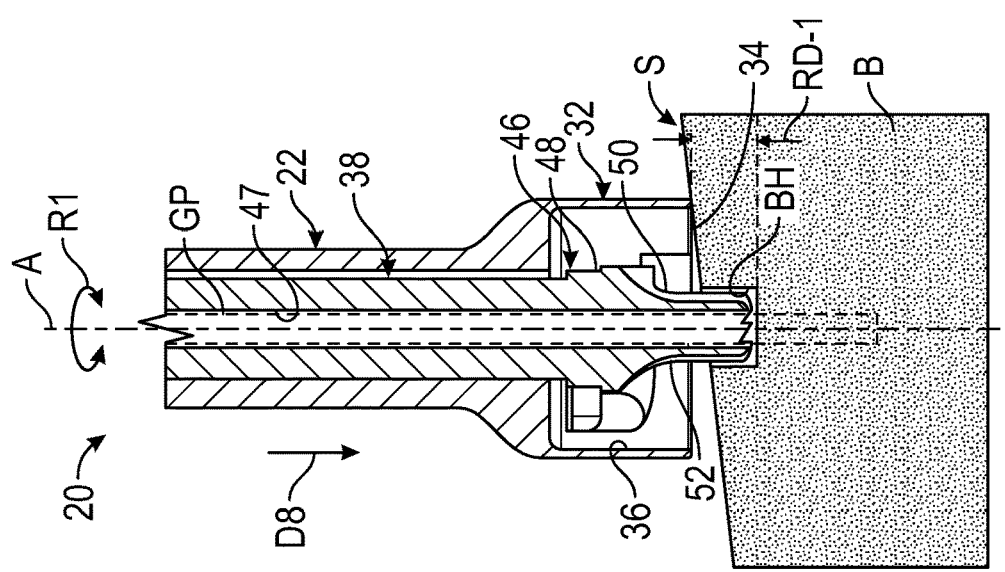

At step 704, the surgeon or operator sets a position of the reaming head 46 according to the selected reaming depth RD (indicated at RD-1 to RD-3 in FIGS. 16-18) corresponding to or otherwise based on the information determined at step 702. FIG. 33 illustrates a first (e.g., minimum) reaming depth RD-1. The reaming portion 48 can be partially (see, e.g., FIG. 3) or completely (see, e.g., FIG. 33) received in the reaming cavity 36 when set at the first reaming depth RD-1. FIG. 34 illustrates a second (e.g., intermediate) reaming depth RD-2. FIG. 35 illustrates a third (e.g., maximum) reaming depth RD-3.

Step 704 can include setting the lock mechanism 54 of the reaming assembly 20 in the macro adjustment mode at step 704A. Step 704A can include moving the macro switch 68 such that the lock threading LT disengages with the shaft threading ST, as illustrated in FIGS. 7-9. Step 704A can include translating the reaming head 46 relative to a distal end of the housing 22 in response to sliding the housing 22 along the drive shaft 38 in the direction D6 (FIG. 3) in the macro adjustment mode to perform a macro (e.g., relative large) adjustment of the reaming depth RD.

Step 704 can include setting the lock mechanism 54 in the micro adjustment mode at step 704B. Step 704B can include moving lock threading LT into engagement with the shaft threading ST and sliding the micro switch 66 across the macro switch 68 such that the micro switch 66 disengages the drive shaft 38, as illustrated by FIGS. 5-6.

Step 704B can include translating the reaming head 46 relative to the terminal end 34 of the housing 22 in the direction D5 (FIG. 2) to set the reaming depth RD in response to relative rotation between the hood 32 and reaming head 46 in the micro adjustment mode. The surgeon or operator may rotate the lock mechanism 54 or housing 22 about the drive shaft 38, for example. Step 704B can be utilized to perform a micro (e.g., relative small) adjustment of the reaming depth RD. Translating the reaming head 46 at steps 704A and/or 704B can include moving a portion of the cutting teeth 52 relative to the hood 32 in the micro and/or macro adjustment modes.

Step 704 can include setting the lock mechanism 54 in the locked mode at step 704C to block or otherwise limit relative rotation between the housing 22 and the reaming head 46. In the locked mode, the drive shaft 38 and housing 22 are locked relative to each other. Step 704C can include sliding the micro switch 66 across the macro switch 68 such that the micro switch 66 engages the drive shaft 38, as illustrated by FIG. 10. In the locked mode, the housing 22 can rotate together with the drive shaft 38.

Referring to FIGS. 33-35, with continuing reference to FIG. 32, the reaming assembly 20 is positioned at a surgical site S at step 706. The lock mechanism 54 is omitted for illustrative purposes. In an embodiment, the surgical site S is a glenoid of a shoulder joint. However, the method could be performed to repair defects in various other tissue within the scope of this disclosure. In other words, this disclosure is in no way limited to repairing bone defects of the glenoid. FIGS. 33-35 illustrate the reaming head 46 set according to three exemplary reaming depths RD-1 to RD-3. Step 706 can include positioning the reaming assembly 20 relative to a guide pin GP (shown in dashed lines for illustrative purposes). The guide pin GP may be positioned at least partially in the inner bore 47 of the drive shaft 38.

Figure 36:
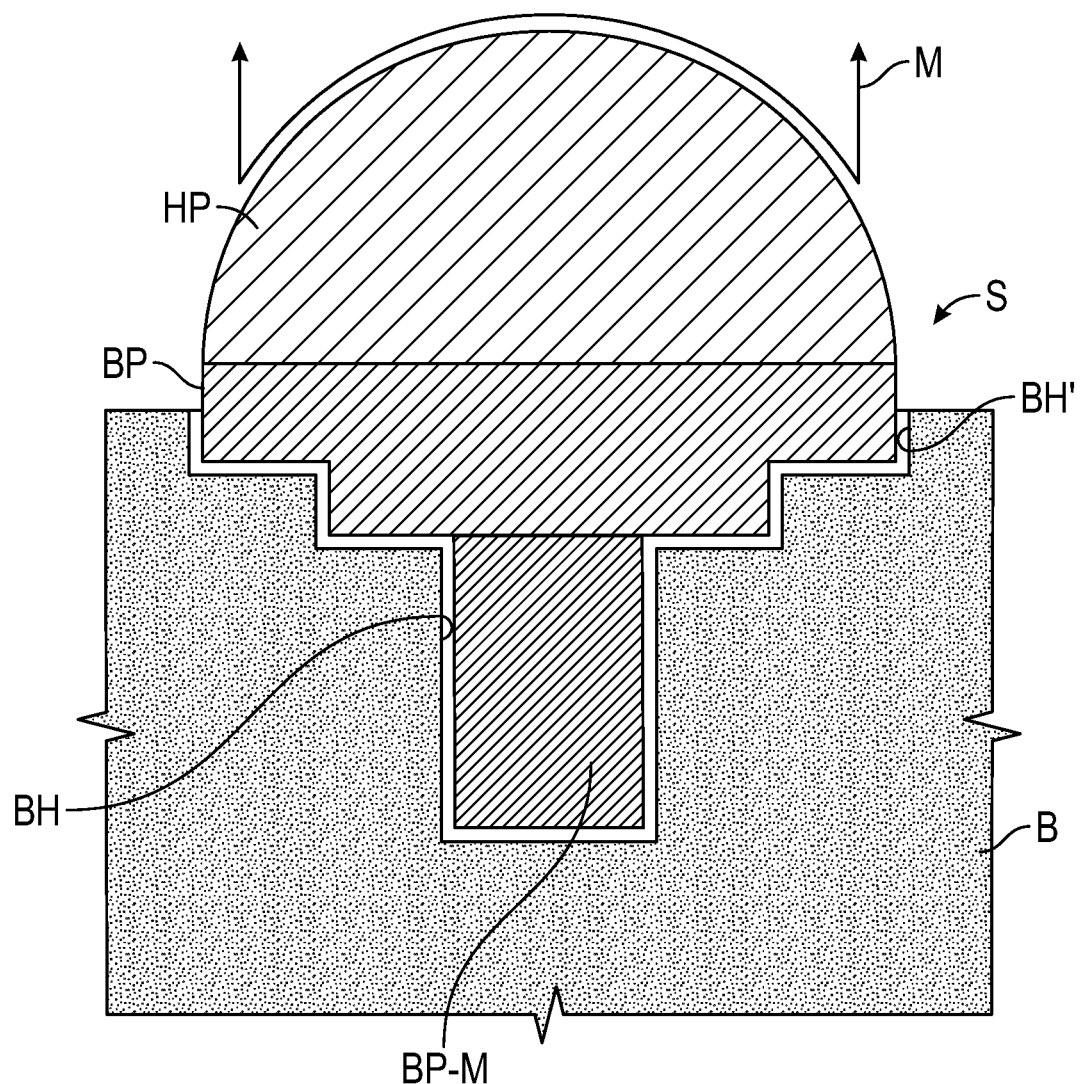
FIG. 36 illustrates an implant positioned at the surgical site of FIG. 35.

At step 708, the surgical site S may be prepared for receiving a bone graft, or an implant such as a bone plate BP (FIG. 36). The surgeon or operator advances the reaming assembly 20 along the guide pin GP toward a surface of the surgical site S. The reaming head 46 is driven by the drive shaft 38 to form at least one recess or bone hole BH during a first (e.g. primary) ream by removing tissue such as bone B at the surgical site S. The hole BH may be formed to remove tissue from a defect in the bone B. Step 708 includes rotating the reaming head 46 rotated to remove bone B in response to rotating the drive shaft 38 in the direction R1 about the longitudinal axis A and/or guide pin GP. Step 708 includes moving the assembly 20 in a direction D8 until the terminal end 34 along the hood 32 contacts a surface of the bone B along the surgical site S to limit the reaming depth RD. The hood 32 limits advancement of the reaming head 46 in the direction D8 along the guide pin GP.

At step 710, the reaming assembly 20 is removed from the surgical site S. In embodiments, the method 700 can include positioning a second reaming assembly at the surgical site S at step 712. The second reaming assembly can be utilized to widen a portion of the primary ream along the surgical site S subsequent to removing the reaming assembly 20 at step 710, for example. The second reaming assembly can include reaming assembly 120 and/or 220. At step 714, additional tissue is removed from the surgical site S to form an enlarged or widen a recess or bone hole BH' (shown in dashed lines in FIG. 36 for illustrative purposes) during a second (e.g. secondary) ream. At step 716, the second reaming assembly is removed from the surgical site S.

Referring to FIG. 36, with continuing reference to FIGS. 33-35, the bone plate BP can be positioned in the bone hole BH/BH' at step 718. The bone plate BP can include an anchoring member BP-M to secure the bone plate BP at the surgical site S. The bone plate BP can have a geometry complementary to the reaming portions 48/148/248, and the anchoring member BP-M can have a geometry complementary to the nose portions 50/150/150 of the reaming assemblies 20/120/220.

A head portion or glenosphere HP can be secured to the bone plate BP to provide an articulating surface for mating with an opposed articulating member M. The articulating member M can be an implant secured to the humerus, for example. In other embodiments, the bone plate BP provides the articulating surface.

The novel devices and methods of this disclosure provide versatility in dimensioning or shaping a recess at a surgical site. The disclosed reaming assemblies can be utilized to form a recess or bone hole at the surgical site and provides improved depth control to more closely approximate a dimension of a bone surface, such as a bone void, which can lead to improved healing at the surgical site. The disclosed depth gauge assemblies and system can be utilized to determine a dimension of a defect, contour or topology of along a surgical site, which can be utilized to more closely approximate dimension(s) and/or select setting(s) utilized for reaming or another operation or surgical procedure, which can lead to improved healing at the surgical site.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A reaming assembly for preparation of a surgical site comprising:
   a housing including a housing body extending along a longitudinal axis between a proximal end portion and a distal end portion, a passageway extending along the longitudinal axis, and a hood extending radially outwardly from the housing body along the distal end portion;
   a rotatable drive shaft received in the passageway;
   a reaming head including cutting teeth, the reaming head coupled to the drive shaft such that the hood is moveable to at least partially surround the cutting teeth; and
   a lock mechanism including a micro lock member and a macro lock member that cooperate to establish at least a locked mode and a micro adjustment mode, the macro lock member including lock threading engageable with shaft threading along the drive shaft such that the reaming head translates along the longitudinal axis in response to relative rotation between the housing and the drive shaft in the micro adjustment mode, the micro lock member disengageable with the drive shaft to permit relative rotation between the housing and the drive shaft in the micro adjustment mode, and the micro lock member engageable with the drive shaft to block relative rotation between the housing and the drive shaft in the locked mode.

2. The assembly as recited in claim 1, wherein the reaming head includes a reaming portion extending outwardly from a nose portion, and the cutting teeth extend along both the reaming and nose portions.

3. The assembly as recited in claim 2, wherein the hood is dimensioned to surround a portion of the cutting teeth along the reaming portion, and the nose portion is dimensioned to extend outwardly from the hood in response to translation of the reaming head along the longitudinal axis in at least the micro adjustment mode.

4. The assembly as recited in claim 1, wherein the micro lock member and the macro lock member cooperate to establish a macro adjustment mode, and the macro lock member is moveable to cause the lock threading to disengage the shaft threading such that the reaming head translates along the longitudinal axis in response to sliding the housing along a length of the drive shaft in the macro adjustment mode.

5. The assembly as recited in claim 4, wherein the macro lock member includes a carrier body having a shaft passage and a lock cavity, the lock threading extends along the shaft passage, the drive shaft is slidably received in the shaft passage such that the shaft threading faces the lock threading, and the micro lock member includes a lock body slidably received in the lock cavity.

6. The assembly as recited in claim 5, wherein the lock body includes a flat portion dimensioned to engage a flat portion along the drive shaft in the micro adjustment and locked modes, and the flat portion of the drive shaft extends across a length of the shaft threading.

7. The assembly as recited in claim 5, further comprising a first spring member between the housing and the carrier body, wherein the housing includes a carrier slot dimensioned to slidably receive the carrier body, and the first spring member is dimensioned to bias the lock threading into engagement with the shaft threading in the micro adjustment and locked modes.

8. The assembly as recited in claim 5, further comprising a retention member slidably received in a retention cavity of the carrier body, and wherein the retention member engages a first recess of the lock body to set a first position of the lock body in the micro adjustment mode, and the retention member engages a second recess of the lock body to set a second position of the lock body in the macro adjustment and locked modes.

9. A kit for preparation of a surgical site comprising:
   a reaming assembly comprising:
      a housing including a housing body extending along a first longitudinal axis between a proximal end portion and a distal end portion, a reaming cavity extending inwardly from a terminal end of the distal end portion, and a passageway extending along the first longitudinal axis between the proximal end portion and the reaming cavity, and a carrier slot extending across the passageway;
      a rotatable drive shaft received in the passageway, and the drive shaft including shaft threading;
      a reaming head coupled to the drive shaft, and the reaming head including cutting teeth at least partially received in the reaming cavity; and
      a lock mechanism including a macro switch and a micro switch configured to set a reaming depth of a range of reaming depths established between the reaming head and the housing, the macro switch including a lock cavity and lock threading extending along a shaft passage, the macro switch slidably received in the carrier slot, the micro switch slidably received in the lock cavity such that the micro switch selectively engages the drive shaft to limit relative rotation, and the drive shaft slidably received in the shaft passage such that the lock threading selectively engages the shaft threading.

10. The kit as recited in claim 9, wherein:
   the macro switch and the micro switch cooperate to establish at least a micro adjustment mode and a macro adjustment mode;
   the lock threading engages the shaft threading such that the reaming head translates along the first longitudinal axis in response to relative rotation between the lock threading and the shaft threading in the micro adjustment mode; and the lock threading disengages the shaft threading such that the reaming head translates along the first longitudinal axis in response to sliding the housing along a length of the drive shaft in the macro adjustment mode.

11. The kit as recited in claim 10, wherein:
the macro switch and the micro switch cooperate to establish a locked mode;
the drive shaft includes an interruption extending across the shaft threading; and
the micro switch is dimensioned to disengage the interruption in the macro adjustment mode and is dimensioned to engage the interruption to block relative rotation between the housing and the drive shaft in the locked mode.

12. The kit as recited in claim 9, wherein:
the macro switch and the micro switch cooperate to establish a locked mode;
the micro switch disengages the drive shaft to permit relative rotation between the housing and the drive shaft in the micro adjustment mode;
the micro switch engages the drive shaft to block relative rotation between the housing and the drive shaft in the locked mode;
the macro switch includes a retention cavity dimensioned to slidably receive a retention member; and
the retention member is dimensioned to set a first position of the micro switch in the micro adjustment mode, and the retention member is dimensioned to set a second position of the micro switch in the macro adjustment and locked modes.

13. The kit as recited in claim 9, further comprising a depth gauge for determining a dimension of a surgical site, wherein the depth gauge comprises:
a gauge housing extending along a second longitudinal axis between proximal and distal end portions of the gauge housing;
a depth indicator aligned with a depth ruler, the depth ruler dimensioned with respect to the range of the reaming depths established between the reaming head and the housing; and
at least one control member extending outwardly from the distal end portion of the gauge housing, wherein the depth indicator is moveable relative to the depth ruler in response to relative movement between the at least one control member relative to the gauge housing.

14. The kit as recited in claim 13, wherein:
the depth gauge includes an actuation shaft extending along the second longitudinal axis;
the at least one control member includes an array of control legs outwardly biased relative to the distal end portion of the gauge housing; and
the actuation shaft is configured to set a position of the depth indicator relative to the depth ruler based on a longitudinally outermost position of the array of control legs relative to the second longitudinal axis.

15. A method of preparing a surgical site in bone comprising:
setting a lock mechanism in a micro adjustment mode;
translating a reaming head relative to a distal end of a housing to set a reaming depth in response to relative rotation between the housing and the reaming head in the micro adjustment mode; and
setting the lock mechanism in a locked mode to block relative rotation between the housing and the reaming head.

16. The method as recited in claim 15, wherein:
the reaming head includes a reaming portion extending outwardly from a nose portion, and cutting teeth extend about both the reaming and nose portions;
the housing includes a hood dimensioned to surround a portion of the cutting teeth at the distal end; and
the translating step includes moving the portion of the cutting teeth relative to the hood in the micro adjustment mode.

17. The method as recited in claim 16, wherein the reaming head is coupled to a cannulated drive shaft including an inner bore, and further comprising:
positioning a guide pin at least partially in the inner bore; and
rotating the reaming head about the guide pin to remove bone along the surgical site.

18. The method as recited in claim 15, wherein:
the reaming head is coupled to a drive shaft;
the lock mechanism includes a macro switch and a micro switch; and
the step of setting the lock mechanism in the micro adjustment mode includes moving lock threading of the macro switch into engagement with shaft threading of the drive shaft and includes sliding the micro switch across the macro switch such that the micro switch disengages the drive shaft.

19. The method as recited in claim 18, wherein the step of setting the lock mechanism in the locked mode includes sliding the micro switch across the macro switch such that the micro switch engages the drive shaft.

20. The method as recited in claim 18, further comprising:
setting the lock mechanism in a macro adjustment mode, including moving the macro switch such that the lock threading disengages with the shaft threading; and
translating the reaming head relative to the distal end of the housing in response to sliding the housing along the drive shaft in the macro adjustment mode.

21. The method as recited in claim 15, further comprising:
selecting the reaming depth based on a geometry of the housing and a profile of the surgical site.

22. The method as recited in claim 15, wherein the step of selecting the reaming depth includes positioning a depth gauge relative to the surgical site, moving a control member relative to a gauge housing of the depth gauge in response to the control member contacting a surface along the surgical site, and setting a position of a depth indicator relative to a depth ruler based on a position of the control member, the reaming depth based on the position of the depth indicator.

* * * * *

UNITED STATES PATENT AND TRADEMARK OFFICE
CERTIFICATE OF CORRECTION

| | |
|---|---|
| PATENT NO. | : 11,160,562 B2 |
| APPLICATION NO. | : 16/738005 |
| DATED | : November 2, 2021 |
| INVENTOR(S) | : Rudraksh Khosla et al. |

It is certified that error appears in the above-identified patent and that said Letters Patent is hereby corrected as shown below:

On the Title Page

Item (72) Inventors: Line 6; replace "Tyler Clevett," with --James Tyler Clevett,--

Signed and Sealed this
Eighteenth Day of October, 2022

Katherine Kelly Vidal
*Director of the United States Patent and Trademark Office*